US007888059B2

(12) United States Patent
Karlish et al.

(10) Patent No.: US 7,888,059 B2
(45) Date of Patent: Feb. 15, 2011

(54) HIGHLY PURIFIED AND STABILIZED NA,K-ATPASE ISOFORMS AND METHODS OF PRODUCING SAME

(75) Inventors: Steven J. D. Karlish, Rechovot (IL); Haim Garty, Rechovot (IL); Yael Lifshitz, Rechovot (IL); Rivka Goldschleger, Jerusalem (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 451 days.

(21) Appl. No.: 11/905,833

(22) Filed: Oct. 4, 2007

(65) Prior Publication Data
US 2008/0199895 A1 Aug. 21, 2008

Related U.S. Application Data

(60) Provisional application No. 60/849,441, filed on Oct. 5, 2006.

(51) Int. Cl.
*C12Q 1/34* (2006.01)
*C07K 1/00* (2006.01)
(52) U.S. Cl. .......................................... 435/18; 530/350
(58) Field of Classification Search .................. 435/18; 530/350
See application file for complete search history.

(56) References Cited

PUBLICATIONS

Bers "Cardiac Excitation-Contraction Coupling", Nature, 415: 198-205, Jan. 10, 2002.
Bitter "Heterologous Gene Expression in Yeast", Methods in Enzymology, 152(Chap.70): 673-684, 1987.
Bitter et al. "Expression and Secretion Vectors for Yeast", Methods in Enzymology, 153(Chap.33): 516-544, 1987.
Cohen et al. "Purification of Na+, K+ -ATPase Expressed in Pichia Pastoris Reveals an Essential Role of Phospholipid-Protein Interactions", The Journal of Biological Chemistry, 280(17); 16610-16618, Apr. 29, 2005.
Cornelius "Cholesterol Modulation of Molecular Activity of Reconstituted Shark Na+, K+ -ATPase", Biochimica et Biophysica Acta, 1235: 205-212, 1995.
Cornelius "Modulation of Na, K-ATPase and Na-ATPase Activity by Phospholipids and Cholesterol. I. Steady-State Kinetics", Biochemistry, 40(30); 8842-8851, 2001.
Crambert et al. "New Molecular Determinants Controlling the Accessibility of Quabain to Its Binding Site in Human Na,K-ATPase α Isoforms", Molecular Pharmacology, 65(2): 335-341, 2004.
Crambert et al. "Transport and Pharmacological Properties of Nine Different Human Na,K-ATPase Isozymes", The Journal of Biological Chemistry, 275(3): 1976-1986, Jan. 21, 2000.
Ferrari et al. "PST2238: A New Antihypertensive Compound That Antagonizes the Long-Term Pressor Effect of Ouabain", The Journal of Pharmacology and Experimental Therapeutics, JPET, 285(1): 83-94, 1998.

Ferrari et al. "Rostafuroxin: An Ouabain Antagonist That Corrects Renal and Vascular Na+ -K+ -ATPase Alterations in Ouabain and Adducin-Dependent Hypertension", American Journal of Physiology—Regulatory, Integrative and Comparative Physiology, 290: R529-R535, 2006.
Hartmanis et al. "Solubilization of A Membrane-Bound Diol Dehydratase With Retention of EPR G=2.02 Signal By Using 2-(N-Cyclohexylamino)Ethanesulfonic Acid Buffer", Proc. Natl. Acad. Sci. USA, 84: 76-79, Jan. 1987.
Hayashi et al. "Minimum Enzyme Unit for Na+/K+ -ATPase Is the αβ-Promoter. Determination by Low-angle Laser Light Scattering Photometry Coupled With High-Performance Gel Chromatography for Substantially Simultaneous Measurement of ATPase Activity and Molecular Weight", Biochimica et Biophysica Acta, 983: 217-229, 1989.
Jørgensen "Purification of Na+,K+ -ATPase: Enzyme Sources, Preparative Problems, and Preparation From Mammalian Kidney", Methods in Enzymology, 156(2): 29-43, 1988.
Jørgensen et al. "Role of Conserved TGDGVND-Loop in Mg2+ Binding, Phosphorylation, and Energy Transfer in Na,K-ATPase", Journal of Bioenergetics and Biomembranes, 35(5): 367-377, Oct. 2001.
Juhaszova et al. "Distinct Distribution of Different Na+ Pump α Subunit Isoforms in Plasmalemma", Annals New York Academy of Sciences, 834: 524-536, 1997.
Lifshitz et al. "Functional Interactions of Phospholemman (PLM) (FXYD1) With Na+,K+ -ATPase. Purification of α1/β1/PLM Complexes Expressed in Pichia Pastoris", The Journal of Biological Chemistry, 281(23): 15790-15799, Jun. 9, 2006.
Müller-Ehmsen et al. "Ouabain and Substrate Affinities of human Na+ -K+ -ATPase α1β1, α2β1 and α3β1 When Expressed Seperately in Yeast Cells", American Journal of Physiology—Cell Physiology, 281: C1355-C1364, Oct. 2001.
Specht et al. "Two Different Na,K-ATPases in the Optic Nerve: Cells of Origin and Axonal Transport", Proc. Natl. Acad. Sci. USA, 81: 1234-1238, Feb. 1984.
Strugatsky et al. "Expression of Na+,K+ -ATPase in Pichia Pastoris. Analysis of Wild Type and D369N Mutant Proteins by Fe2+ -Catalyzed Oxidative Cleavage", The Journal of Biological Chemistry, 278(46): 46064-46073, Nov. 14, 2003.
Sweadner "Isozymes of the Na+/K+ -ATPase", Biochimica et Biophysica Acta, 988: 185-220, 1989.
Sweadner "Two Molecular Froms of (Na+ + K+)-Stimulated ATPase in Brain. Separation, and Difference in Affinity for Strophanthidin", The Journal of Biological Chemistry, 254(13): 6060-6067, Jul. 10, 1979.

(Continued)

*Primary Examiner*—Maryam Monshipouri

(57) ABSTRACT

A composition of matter comprising active Na,K-ATPase is disclosed, each Na,K-ATPase comprising an α and β subunit, the Na,K-ATPase being at least 85% purified. Methods of purifying same and uses thereof are also disclosed.

**18 Claims, 18 Drawing Sheets
(16 of 18 Drawing Sheet(s) Filed in Color)**

OTHER PUBLICATIONS

Tian et al. "Signal-Transducing Function of Na+ -K+ -ATPase Is Essential for Ouabain's Effect on [Ca2+]I in Rat Cardiac Myocytes", American Journal of Physiology—Heart and Circulation Physiology, 281: H1899-H1907, 2001.

Xie et al. "Na+/K+ -ATPase as a Signal Transducer", European Journal of Biochemistry, 269: 2434-2439, Feb. 2002.

Yeagle et al. "Effects of Cholesterol on (Na+,K+)-ATPase ATP Hydrolyzing Activity in Bovine Kidney", Biochemistry, 27: 6449-6452, 1988.

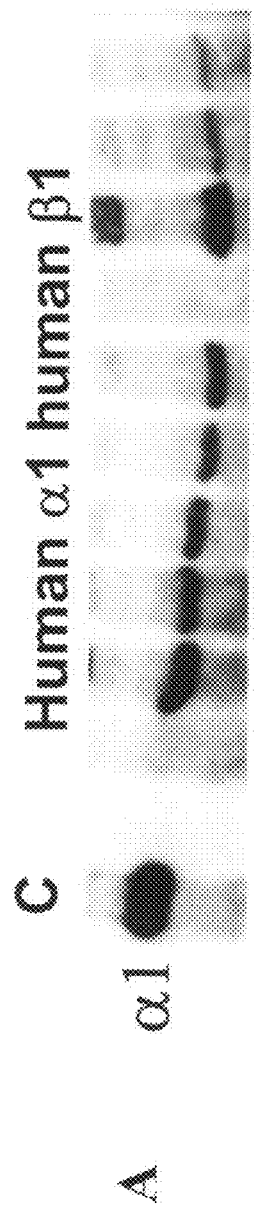
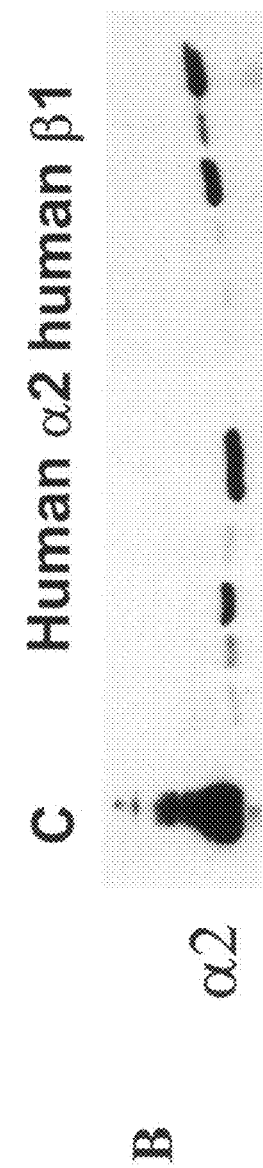
FIGs. 4A-C

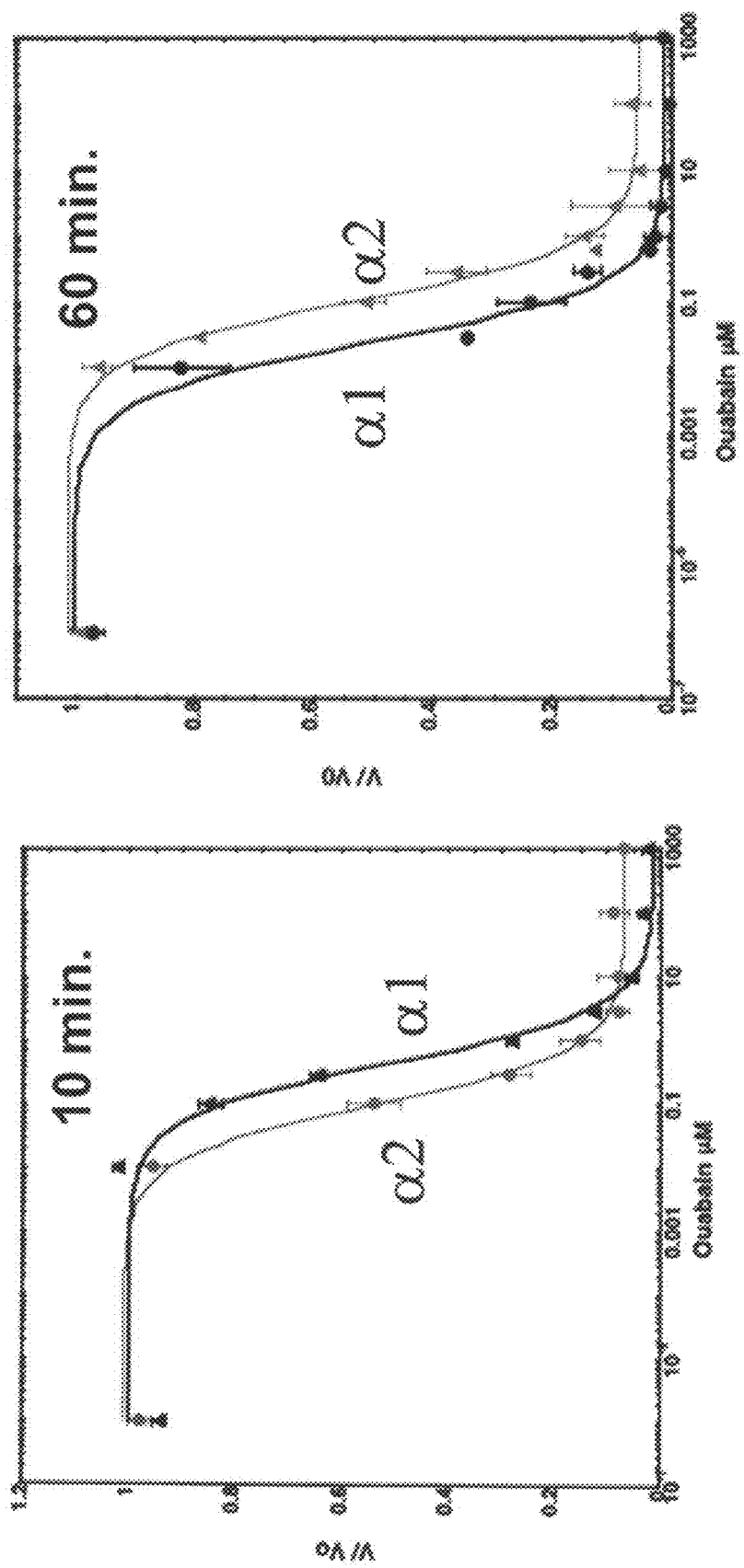
FIGs. 17A-B

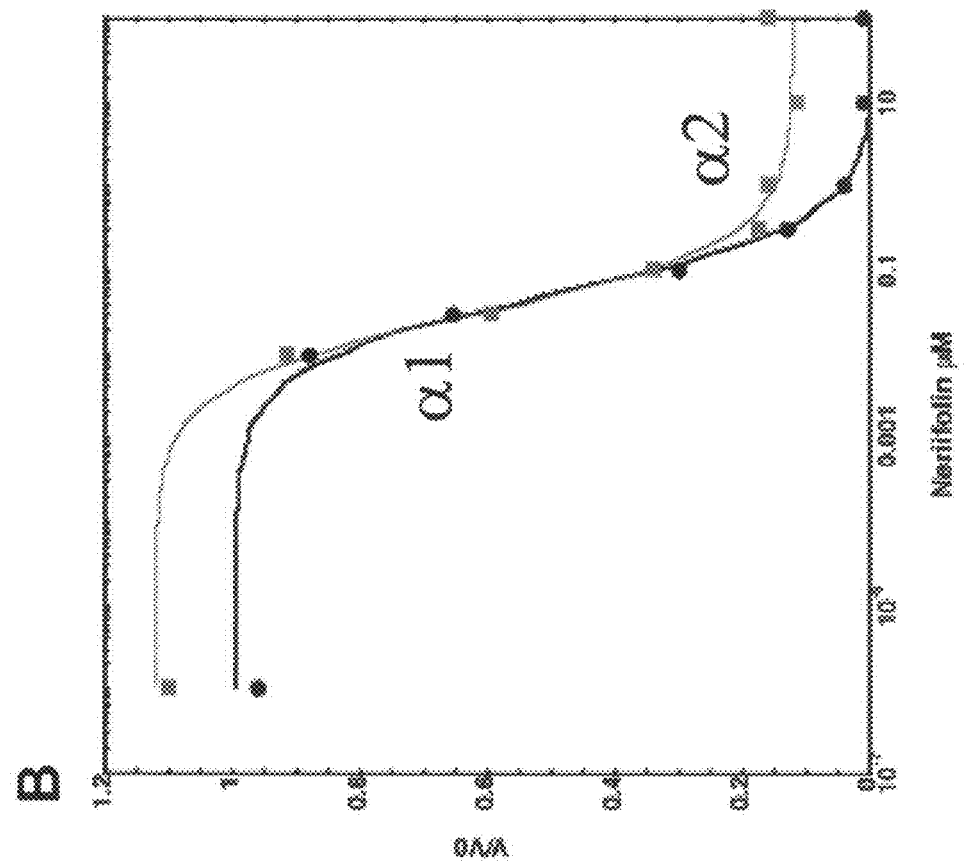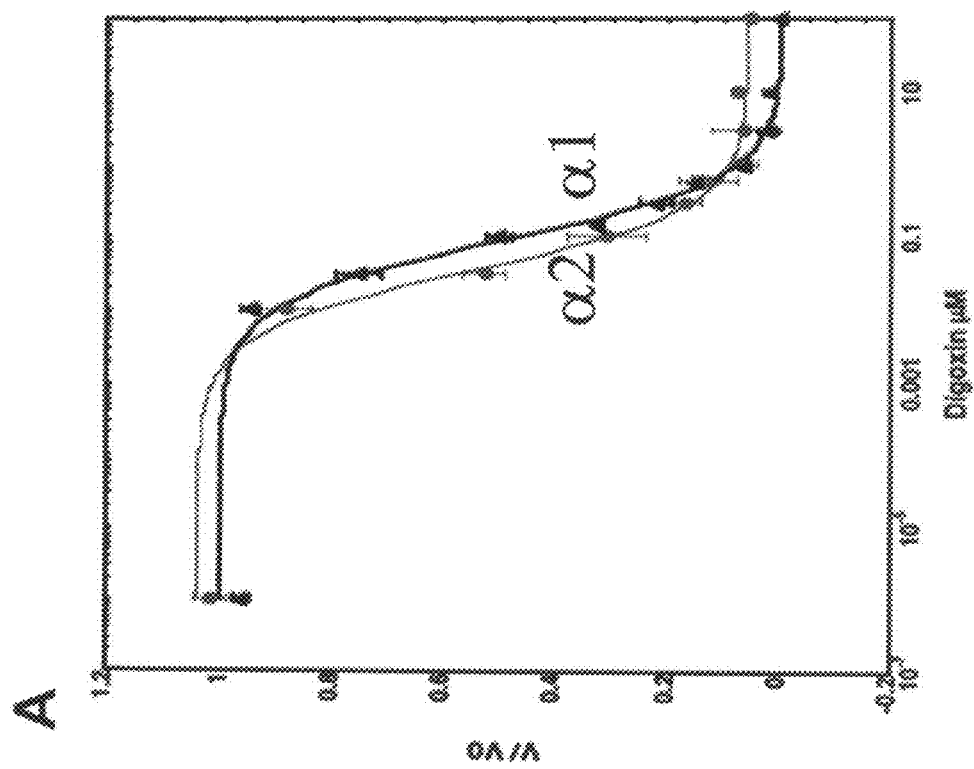
FIGs. 18A-B ously avoided. As
HIGHLY PURIFIED AND STABILIZED NA,K-ATPASE ISOFORMS AND METHODS OF PRODUCING SAME

RELATED APPLICATION

This application claims the benefit of U.S. Provisional Patent Application No. 60/849,441 filed on Oct. 5, 2006, the contents of which are hereby incorporated in its entirety.

FIELD AND BACKGROUND OF THE INVENTION

The present invention relates to purified and stabilized isoforms of Na,K-ATPase and methods of obtaining same.

For over two hundred years the plant-derived digitalis glycosides have been used to treat congestive heart failure. Digoxin, the principal cardiac glycoside (CG) used in clinical practice, has been shown to reduce mortality from congestive heart failure (CHF). However, digoxin has a narrow therapeutic window (particularly in K-depleted patients) and has been shown to induce cardiac arrhythmias.

The mechanism of the positive inotropic effects of cardiac glycosides involves (a) inhibition of the cardiac Na,K-ATPase, (b) reduction of the normal trans-membrane Na gradient (c) functional coupling with the 3Na/Ca exchanger to increase Ca entry into the cell (d) pumping of the excess Ca into the sarcoplasmic reticulum (SR) by the Ca-ATPase (e) release of Ca from SR via ryanodine receptor (RyR) and IP3 Ca channels upon electrical excitation of the muscle and (f) increased force of contraction of cardiac muscle due to the raised cytoplasmic Ca concentration.

The Na,K-ATPase consists of both $\alpha$ and $\beta$ subunits. Four isoforms of a ($\alpha_1$, $\alpha_2$, $\alpha_3$ and $\alpha_4$) and three isoforms of $\beta$ ($\beta_1$, $\beta_2$ and $\beta_3$) are known. Human heart is known to express not only the ubiquitous $\alpha_1$ "house-keeping" isoform but also the $\alpha_2$ and $\alpha_3$ isoforms. In addition, the human heart is known to express $\beta_1$ but not $\beta_2$. This indicates that in humans, the pump complexes are $\alpha_1\beta_1$ $\alpha_2\beta_1$ and $\alpha_3\beta_1$.

It is believed that CG toxicity results from excessive inhibition of Na,K-ATPase, resulting in Ca accumulation in the cell, beyond the capacity of the SR to sequester it. This is termed Ca-overload. As a result of the Ca-overload, the 3Na/Ca exchanger (NCX1) is activated, and because this exchanger is electrogenic the membrane potential is partially depolarized following the normal repolarization phase of the action potential. This is termed delayed after depolarizations (DADS). DADS induce spontaneous firing and unsynchronized heart beats—i.e arrhythmias. Since the $\alpha_1$ isoform is the major form in human heart, while $\alpha_2$ (and $\alpha_3$) are present at lower levels, excessive inhibition is inevitably associated with the housekeeping $\alpha_1$ isoform. Therefore, by avoiding inhibition of $\alpha_1$, and restricting inhibition to a minor fraction of the Na,K-ATPase molecules, excess inhibition of Na,K-ATPase and Ca-overload should be automatically avoided. As mentioned above, in human heart both $\alpha_2$ and $\alpha_3$ isoforms are expressed as well as $\alpha_1$. Thus, in principle, either an $\alpha_2$ or an $\alpha_3$-specific inhibitor could reduce the Ca-overload problem and be a safer inotropic drug.

CG toxicity is exacerbated in patients with depleted serum K, associated with congestive heart failure or following diuretic therapy. Excessive inhibition of the Na,K-ATPase can be the result of diminution of the normal CG-serum K antagonism, which determines the appropriate therapeutic dose of CG (1-2 nM for digoxin). Another aspect of CG toxicity is the fact that CG's dissociate slowly from the Na,K-ATPase, so that the effect of toxic concentrations is not readily reversed. New compounds in which these features differ from those of digoxin, the standard CG in clinical use, either for both isoforms, or in an isoform-specific way, could also be important in the search for a safer CG.

Recent research suggests that in addition to pumping ions, Na(+)/K+-ATPase interacts with neighboring membrane proteins and organized cytosolic cascades of signaling proteins to send messages to the intracellular organelles [Xie and Askari, 2002, Eur J Biochem, 269, 2434-2439]. The likely extracellular physiological stimuli for the signal transducing function of Na+/K+-ATPase are the endogenous ouabain-like hormones, and changes in extracellular K+ concentration. The signaling pathways that are rapidly elicited by the interaction of ouabain with Na(+)/K(+)-ATPase are reported to be independent of changes in intracellular Na(+) and K(+) concentrations, and involve a cascade of events via the EGF receptor/Src and the ERK1/p42/44 MAPK pathways to regulate growth-related gene transcription. It has also been suggested that this pathway is necessary for the inotropic effect of CG's by increasing cytoplasmic Ca (Tian et al., 2001, Am J Physiol Heart Circ Physiol, 281, H1899-1907). Thus, this ouabain-signaling pathway is of interest in relation to long-term growth regulation and cardiac hypertrophy, and in this respect could be another target of novel CG's.

A unique mode of regulation of the Na, K-ATPase has been described recently, involving interactions between the $\alpha/\beta$ complex and the FXYD proteins. The FXYD family consists of seven short single span transmembrane proteins (N terminus extracellular), named after the conserved FXYD motif in the extracellular segment. The FXYD proteins show a tissue-specific expression pattern. Six members of the family, FXYD1 (PLM), FXYD2 ($\gamma$), FXYD3 (Mat-8), FXYD4 (CHIF), FXYD5 (RIC), and FXYD7, are now known to interact specifically with the Na,K-ATPase, and modulate the functional properties. The FXYD proteins are not required for basic pump function, but they act as accessory subunits to the $\alpha$ and $\beta$ subunits, and modulate the kinetic properties in a tissue-specific fashion.

Previous work with human isoforms of Na,K-ATPase expressed in *Xenopus* Oocytes showed that $H^3$-ouabain binds to and dissociates from $\alpha 2$ much faster than to $\alpha 1$ and $\alpha 3$ while equilibrium dissociation constants are fairly similar. Human isoforms have also been expressed in the yeast *S. cerevesiae* (Muller-Ehmsen et al., American J. Physiol Cell Physiol, 281: c1355-C1364, 2001), where roughly similar dissociation constants for $\alpha 1$, $\alpha 2$ and $\alpha 3$ for ouabain were measured. A low expression level of $\alpha 2$ was observed which was explained by instability. Neither the X oocyte nor the *S. cerevesiae* expression systems provide suitable material for large scale screening of inhibitors since the density of the induced Na,K-ATPases was not sufficiently high for purification and thus the induced protein is unstable ($\alpha 2$) (*S. Cerevesiae*), or the electrophysiological measurements are too unwieldy (X. Oocytes). In order to carry out high throughput screens of inhibitors on the different human isoforms, and compare inhibitor properties in detail, availability of purified active and stable Na,K-ATPase isoforms is required.

Porcine Na,K-ATPase has been expressed in the methanotrophic yeast *P. pastoris* (Cohen et al., 2005, J Biol Chem, 280, 16610-16618; Strugatsky et al., 2003, J Biol Chem, 278, 46064-46073). The present inventors showed (Cohen et al., 2005, J Biol Chem, 280, 16610-16618) that following expression of Porcine $\alpha$/his$_{10}$-$\beta$ subunits and solubilization of the yeast membranes in n-dodecyl-$\beta$-maltoside (DDM), detergent-soluble $\alpha$/his$_{10}$-$\beta$ complexes could be purified utilizing a combination of $Ni^{2+}$-NTA bead chromatography and size-exclusion HPLC. The procedure produced 70-80% percent pure porcine Na,K-ATPase. This complex, two-step procedure however is not convenient for producing large quantities of Na,K-ATPase for high through-put screening.

There remains a widely recognized need therefore, and it would be highly advantageous to have simpler methods of expressing and purifying different isoforms of Na,K-ATPases, where the resultant Na,K-ATPases are functional and stable over an extended period of time. In particular it would be advantageous to have purified human isoforms for testing selectivity of inhibitors, since native human tissue is not readily available and cardiac tissue is not suitable for this task because it comprises a mixture of the isoforms.

SUMMARY OF THE INVENTION

According to one aspect of the present invention there is provided composition of matter comprising catalytically active Na,K-ATPase, said Na,K-ATPase comprising an α and β subunit, said Na,K-ATPase being at least 85% purified.

According to another aspect of the present invention there is provided a composition of matter comprising purified catalytically active Na,K-ATPase the Na,K-ATPase comprising an α and β subunit, wherein a half-life for loss of activity at 0° C. of the Na,K-ATPase is at least 15 days.

According to yet another aspect of the present invention there is provided a composition of matter comprising purified catalytically active Na, K-ATPase, and FXYD, wherein the Na,K-ATPase comprises an α and β subunit.

According to still another aspect of the present invention there is provided an isolated cell expressing exogenous Na,K-ATPase, the exogenous Na,K-ATPase comprising an α and β subunit, wherein at least one of the subunits is of human origin and wherein a ouabain binding capacity of the cell is at least 15 pmoles ouabain binding capacity per mg of membrane protein According to an additional aspect of the present invention there is provided a membrane preparation of an isolated cells expressing exogenous Na,K-ATPase, the exogenous Na,K-ATPase comprising an α and β subunit, wherein at least one of the subunits is of human origin and wherein a ouabain binding capacity of the cell is at least 15 pmoles ouabain binding capacity per mg of membrane protein According to yet an additional aspect of the present invention there is provided a method of purifying a Na,K-ATPase, the method comprising:

(a) contacting a yeast membrane preparation comprising the Na,K-ATPase with a divalent metal chelator; and (b) affinity purifying the Na,K-ATPase from the yeast membrane preparation, thereby purifying the Na,K-ATPase.

According to still an additional aspect of the present invention there is provided a method of purifying a poly-histidine tagged Na,K-ATPase, the method comprising immobilizing a membrane preparation which comprises the poly-histidine tagged Na,K-ATPase on a $Co^{2+}$-chelate affinity resin, thereby purifying the poly-histidine tagged Na,K-ATPase.

According to a further aspect of the present invention there is provided a method of identifying an agent capable of regulating an activity of Na,K-ATPase, the method comprising determining an activity of the Na,K-ATPase in the composition of matter comprising catalytically active Na,K-ATPase, said Na,K-ATPase comprising an α and β subunit, said Na,K-ATPase being at least 85% purified, in the presence and absence of the agent, wherein a change in the activity of the Na,K-ATPase is indicative of an agent capable of regulating the activity of the Na,K-ATPase.

According to yet a further aspect of the present invention there is provided a method of identifying an agent capable of regulating an activity of Na,K-ATPase, the method comprising determining an activity of the Na,K-ATPase in the composition of matter comprising purified catalytically active Na,K-ATPase the Na,K-ATPase comprising an α and β subunit, wherein a half-life for loss of activity at 0° C. of the Na,K-ATPase is at least 15 days, in the presence and absence of the agent, wherein a change in the activity of the Na,K-ATPase is indicative of an agent capable of regulating the activity of the Na,K-ATPase.

According to further features in preferred embodiments of the invention described below, the α subunit is selected from the group consisting of an $α_1$ subunit, an $α_2$ subunit and an $α_3$ subunit.

According to still further features in the described preferred embodiments, the β subunit is a $β_1$ subunit or a $β_3$ subunit.

According to still further features in the described preferred embodiments, at least one of the subunits of Na,K-ATPase is of a human origin.

According to still further features in the described preferred embodiments, at least one of the subunits of Na,K-ATPase is of a porcine origin.

According to still further features in the described preferred embodiments, the Na,K-ATPase comprises a human $α_1$ subunit and a porcine $β_1$ subunit.

According to still further features in the described preferred embodiments, the Na,K-ATPase comprises a human $α_2$ subunit and a porcine $β_1$ subunit.

According to still further features in the described preferred embodiments, the Na,K-ATPase comprises a porcine $α_1$ subunit and a porcine $β_1$ subunit.

According to still further features in the described preferred embodiments, the composition further comprises phospholipids According to still further features in the described preferred embodiments, the phospholipids comprise acidic phospholipids.

According to still further features in the described preferred embodiments, the acidic phospholipids comprise at least one saturated and one unsaturated fatty acid side-chain.

According to still further features in the described preferred embodiments, the acidic phospholipids are selected from the group consisting of SOPS, DOPS and POPS.

According to still further features in the described preferred embodiments, the acidic phospholipids are SOPS.

According to still further features in the described preferred embodiments, the composition further comprises cholesterol.

According to still further features in the described preferred embodiments, the composition further comprises FXYD.

According to still further features in the described preferred embodiments, the FXYD is selected from the group consisting of FXYD1, FXYD2, FXYD3, FXYD4, FXYD5 and FXYD7.

According to still further features in the described preferred embodiments, the FXYD is FXYD1.

According to still further features in the described preferred embodiments, a half-life for loss of activity at 0° C. of the Na,K-ATPase is at least 20 days.

According to still further features in the described preferred embodiments, the Na,K-ATPase is at least 85% purified.

According to still further features in the described preferred embodiments, the cell is a yeast cell.

According to still further features in the described preferred embodiments, the method further comprises washing the Co$^{2+}$-chelate affinity resin with a wash solution following the immobilization.

According to still further features in the described preferred embodiments, the wash solution comprises a non-ionic detergent.

According to still further features in the described preferred embodiments, the non-ionic detergent is C12E8 or DDM.

According to still further features in the described preferred embodiments, the wash solution further comprises phospholipids.

According to still further features in the described preferred embodiments, the wash solution further comprises cholesterol.

According to still further features in the described preferred embodiments, the method further comprises contacting the yeast membrane preparation comprising the Na,K-ATPase with FXYD prior to the washing.

According to still further features in the described preferred embodiments, the method further comprises eluting the Na,K-ATPase with an eluting solution following the washing.

According to still further features in the described preferred embodiments, the eluting solution comprises a non-ionic detergent.

According to still further features in the described preferred embodiments, the eluting solution further comprises phospholipids.

According to still further features in the described preferred embodiments, the eluting solution further comprises cholesterol.

According to still further features in the described preferred embodiments, the yeast membrane preparation further comprises a divalent metal chelator.

According to still further features in the described preferred embodiments, the divalent metal chelator is selected from the group comprising EDTA, EGTA and CDTA.

According to still further features in the described preferred embodiments, the divalent metal chelator is EDTA.

According to still further features in the described preferred embodiments, a concentration of the EDTA is less than 100 μM per mg/ml of protein and greater than 10 μM per mg/ml of protein.

According to still further features in the described preferred embodiments, the concentration of EDTA is about 50 μM per mg/ml of protein.

According to still further features in the described preferred embodiments, the method further comprises expressing the Na,K-ATPase in the yeast cells prior to the contacting.

According to still further features in the described preferred embodiments, the method further comprises expressing the Na,K-ATPase in the yeast cells prior to the binding the yeast membrane preparation with the Co$^{2+}$-chelate affinity resin.

According to still further features in the described preferred embodiments, the expressing is effected at less than 30° C.

According to still further features in the described preferred embodiments, when the Na,K-ATPase comprises an $\alpha_2$ subunit and a $\beta_1$ subunit, the expressing is effected at about 20° C.

According to still further features in the described preferred embodiments, the yeast membrane preparation is a *P. pastoris* yeast membrane preparation.

The present invention successfully addresses the shortcomings of the presently known configurations by providing highly purified Na,K-ATPase isoforms, which are both functional and stable over an extended period of time.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one thawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B are photographs of Coomassie-stained gels illustrating the single-step purification of recombinant Na,K-ATPase by BD Talon bead metal affinity chromatography. FIG. 1A: *Pichia pastoris* membranes expressing porcine $\alpha_1\beta_1$ subunits (10 mg) were solubilized and applied to BD-Talon resin (100 μl) in the presence of indicated concentrations of EDTA. Each lane represents 3 μg of eluted protein. NAK—3 μg of purified pig kidney Na,K-ATPase. FIG. 1B: BD-Talon resin bound with porcine $\alpha_1\beta_1$ from 10 mg membranes were incubated with Endo-H (500 units) overnight on ice.

FIGS. 2A-E are photographs and tables illustrating the expression of human $\alpha_1$ and $\alpha_2$ Na,K-ATPase subunits in *Pichia pastoris* membranes.

Figure 3:
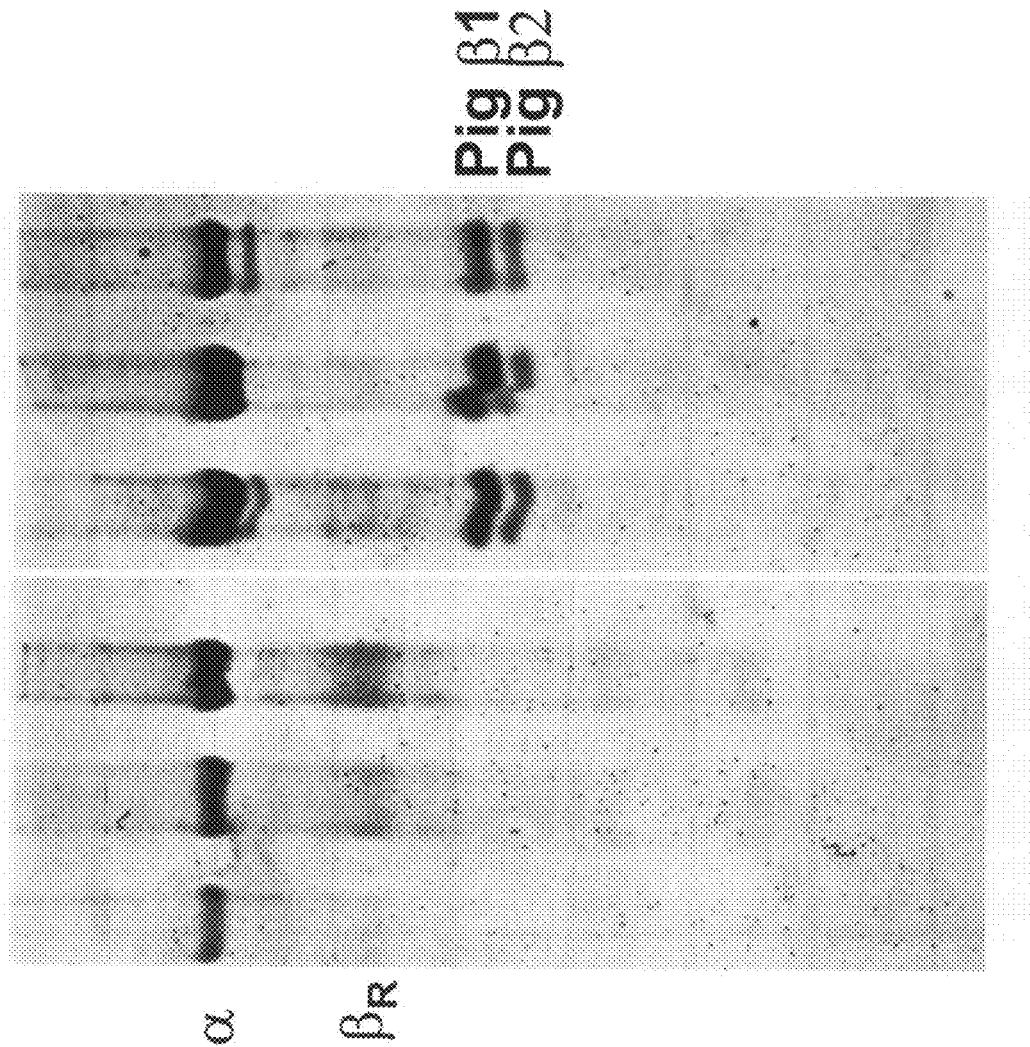

FIG. 3 is a photograph of a Coomassie-stained gel illustrating the purification of both human and porcine Na,K-ATPases.

FIGS. 4A-C are photographs illustrating the expression of all human Na,K-ATPases. FIG. 4A illustrates the expression of all human $\alpha_1\beta_1$ Na,K-ATPase. FIG. 4B illustrates the expression of all human $\alpha_2\beta_1$ Na,K-ATPase. FIG. 4C illustrates the expression of all human $\alpha_1\beta_3$ Na,K-ATPase.

Figure 5:
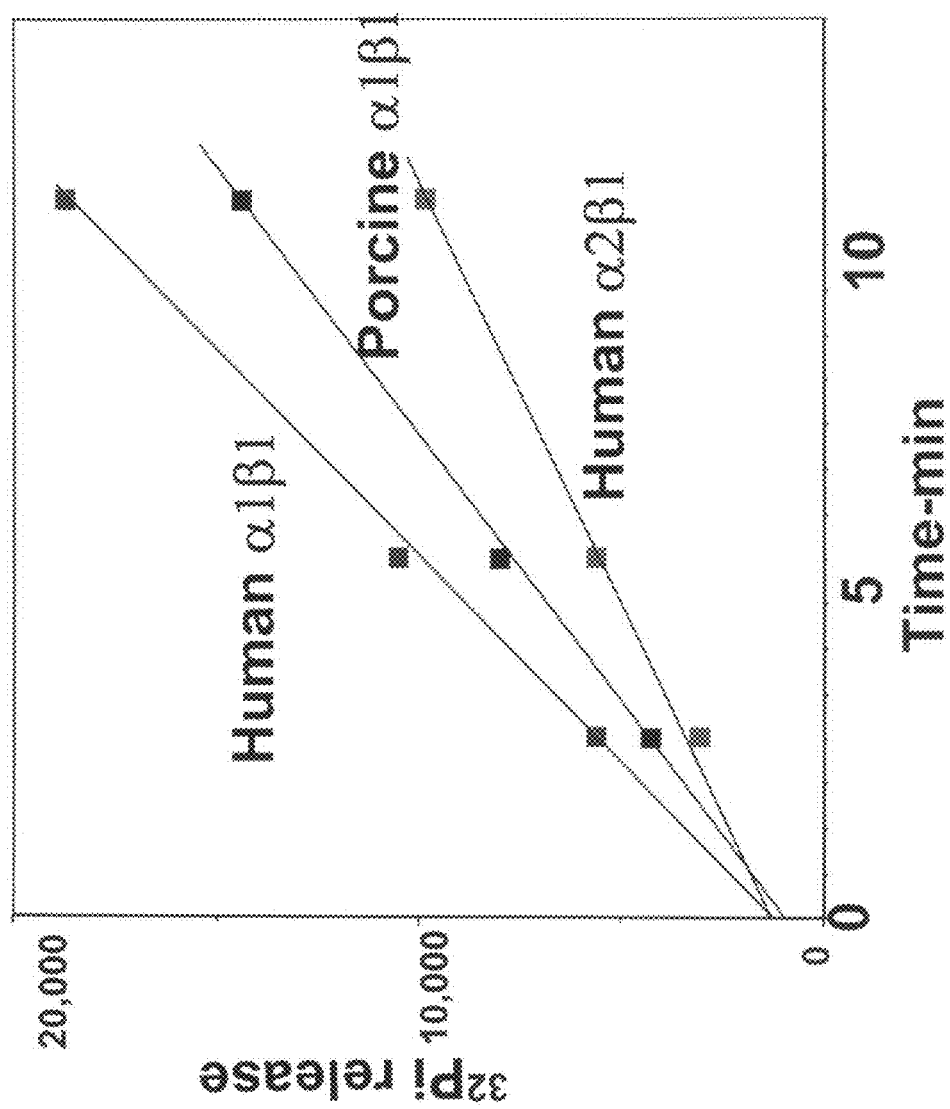

FIG. 5 is a graph illustrating Na,K-ATPase activity of purified human $\alpha_1\beta_1$, porcine $\alpha_1\beta_1$ and human $\alpha_2\beta_1$ complexes.

Figure 6:
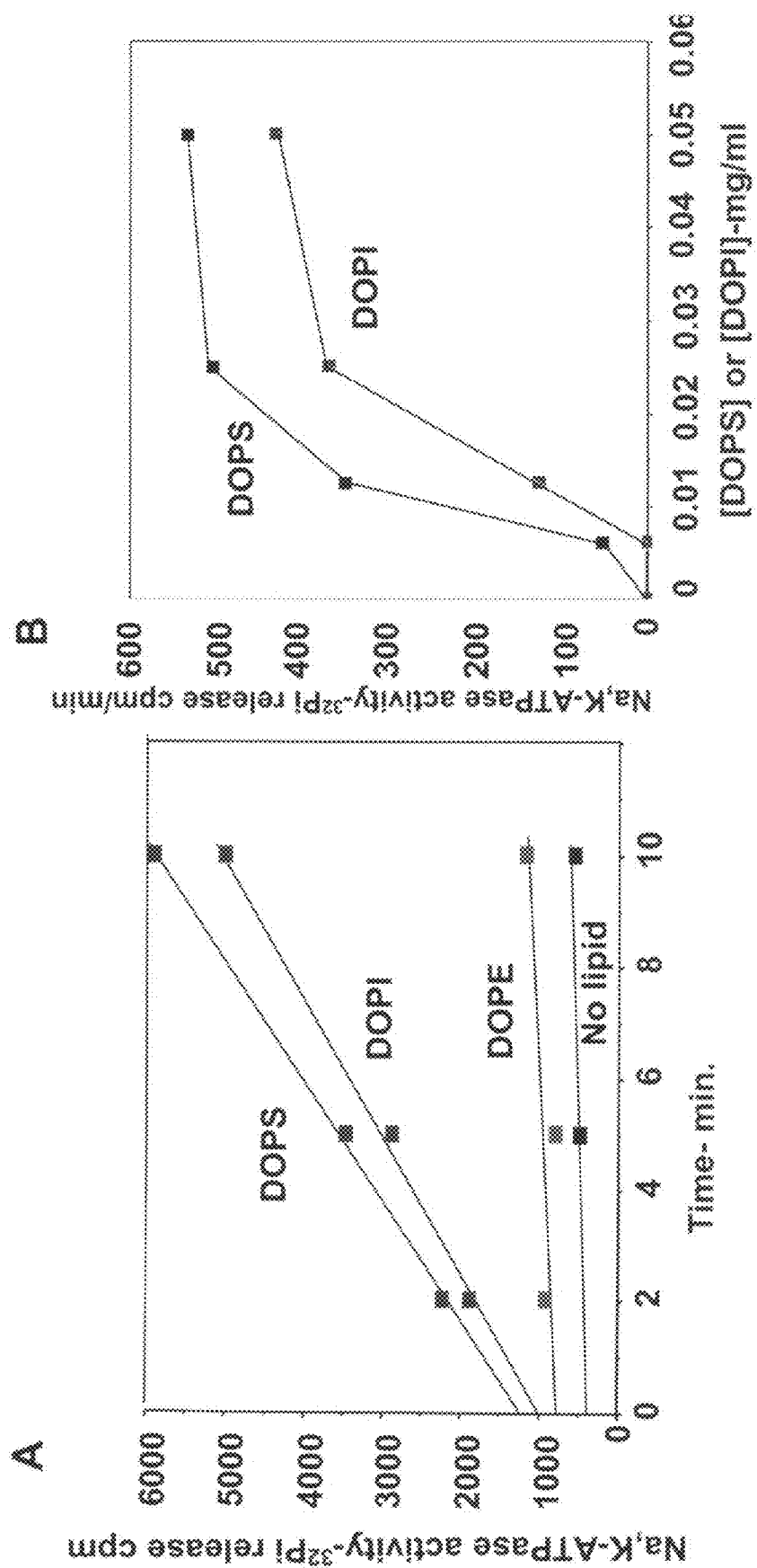

FIGS. 6A-B are graphs illustrating the effect of different phospholipids on Na,K-ATPase activity. FIG. 6A illustrates the effect of different phospholipids over time on Na,K-ATPase activity. FIG. 6B illustrates the effect of increasing quantities of phospholipids on Na,K-ATPase activity.

Figure 7:
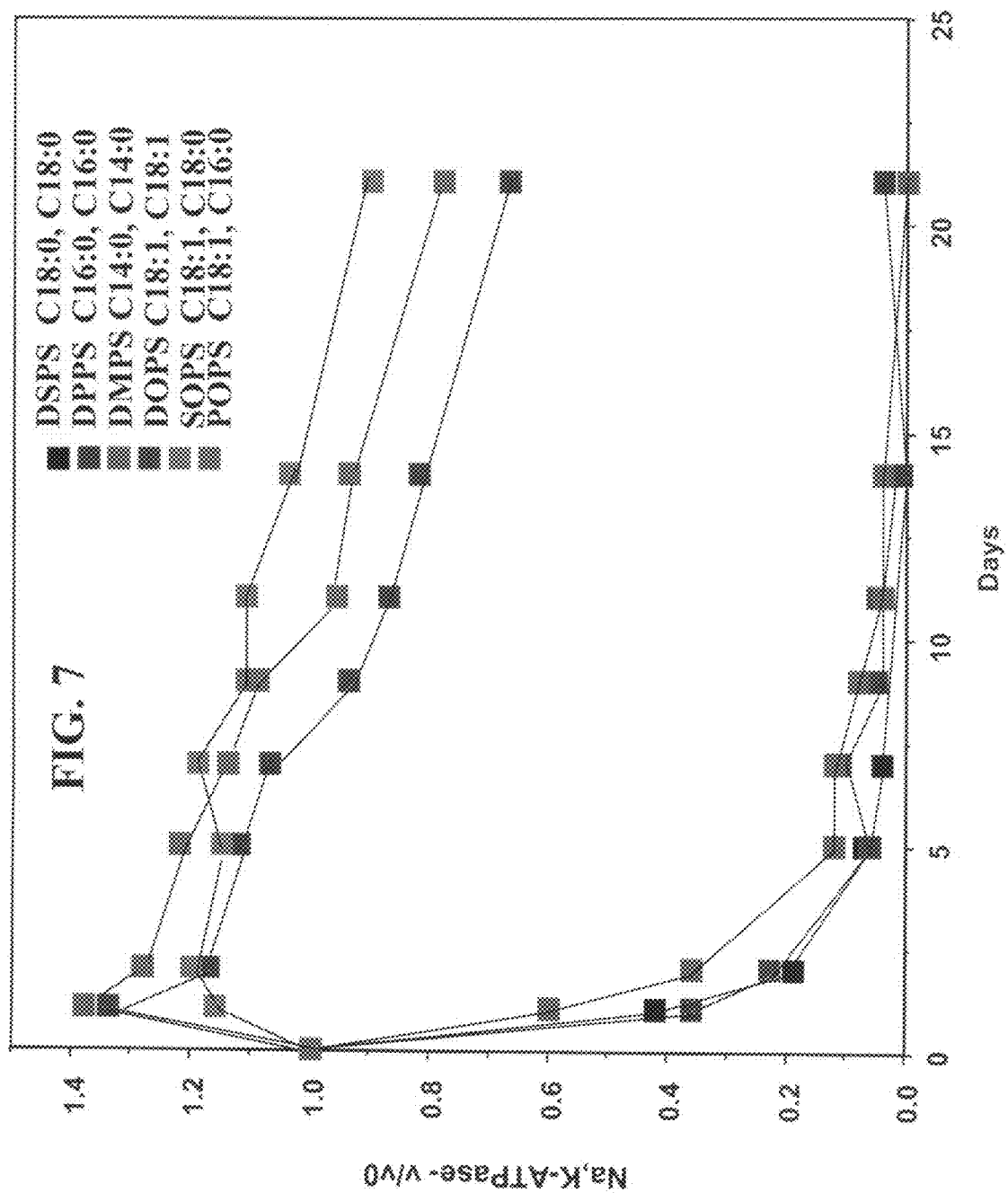

FIG. 7 is a graph illustrating the effect of incorporating at least one unsaturated fatty acid chain into phosphatidyl serine on Na,K-ATPase activity.

FIGS. 8A-B are graphs illustrating the superiority of SOPS in stabilizing both porcine (FIG. 8A) and human (FIG. 8B) $\alpha_1\beta_1$ Na,K-ATPase complexes.

Figure 9:
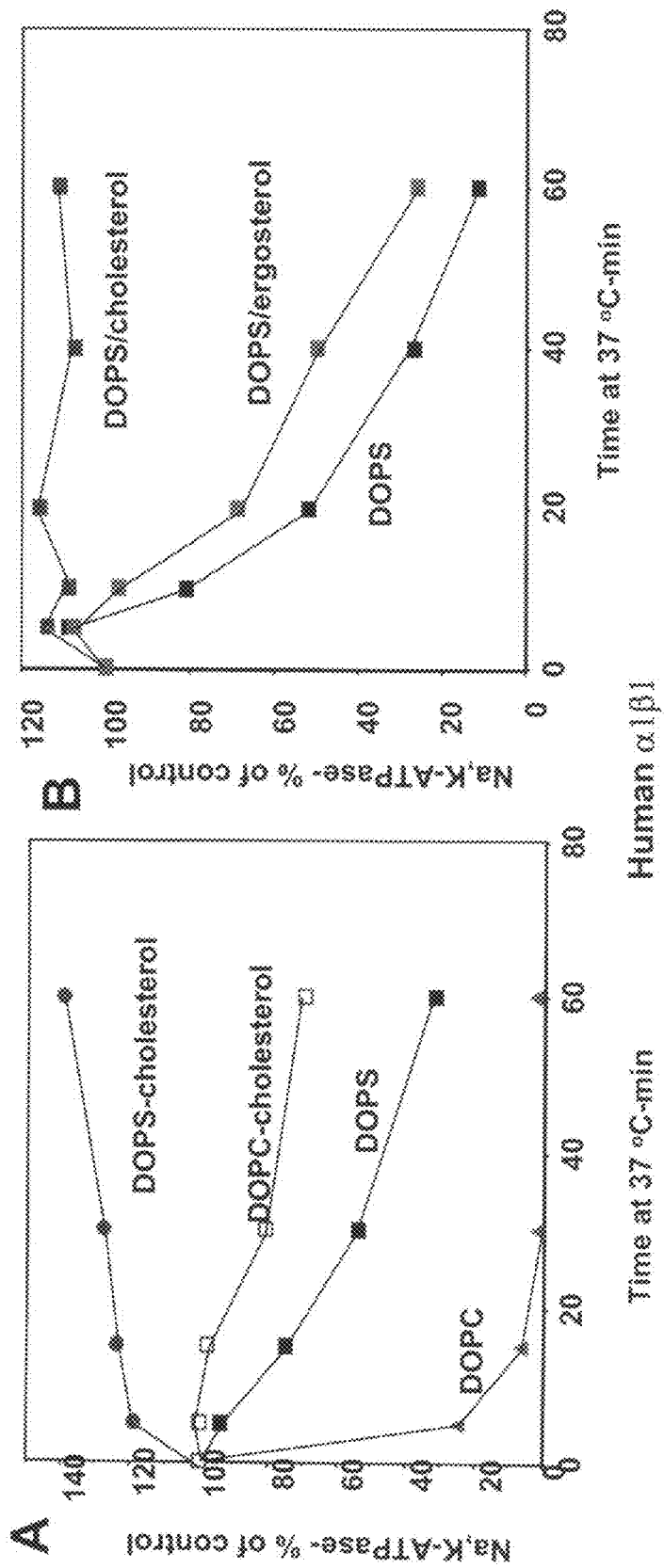

FIGS. 9A-B are graphs illustrating the stabilization of $\alpha_1\beta_1$ Na,K-ATPase complexes by cholesterol at 37° C. FIG. 9C are illustrations of the structures of cholesterol and ergosterol.

Figure 10:
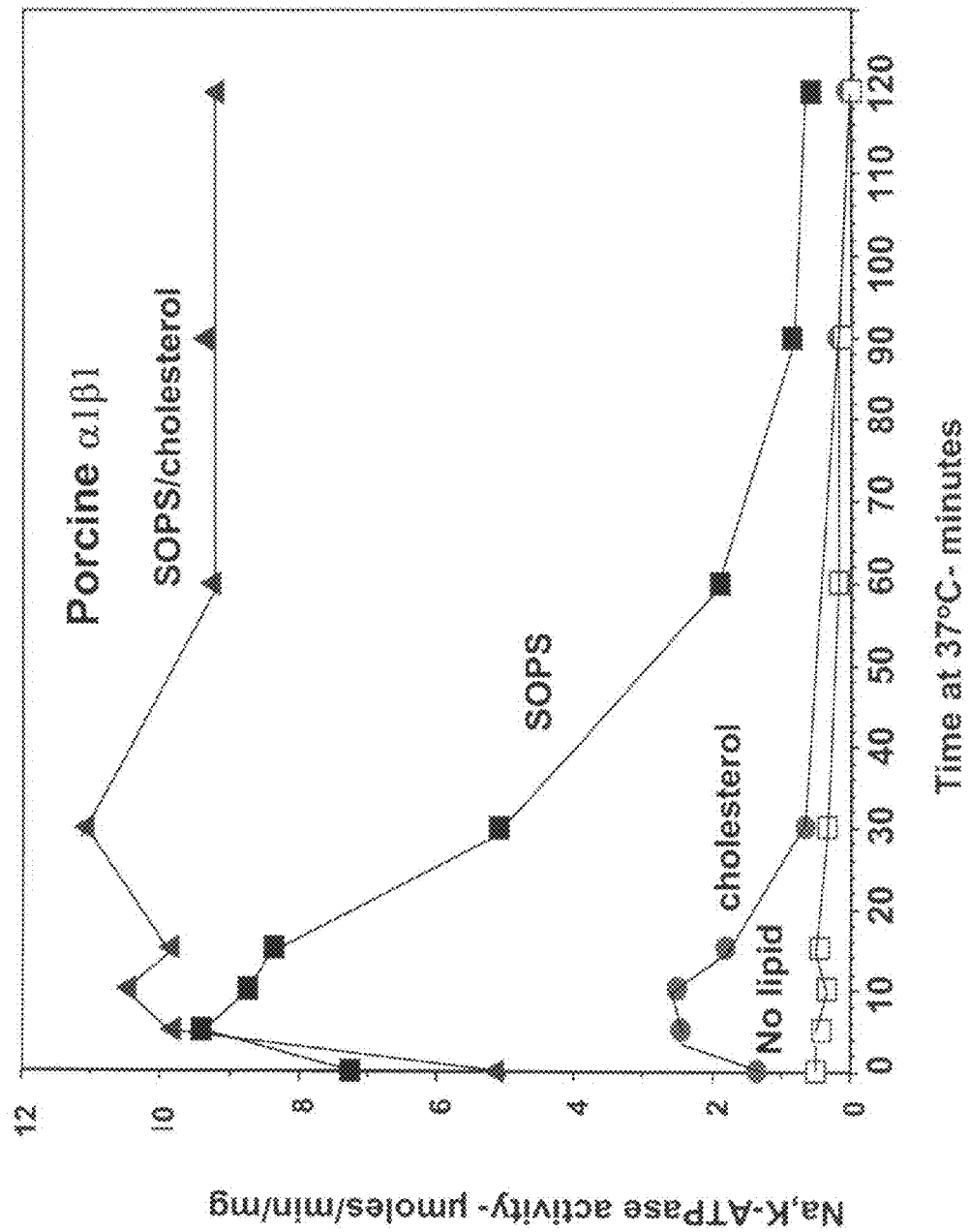

FIG. 10 is a graph illustrating the synergism between SOPS and cholesterol in stabilizing $\alpha_1\beta_1$ at 37° C.

Figure 11:
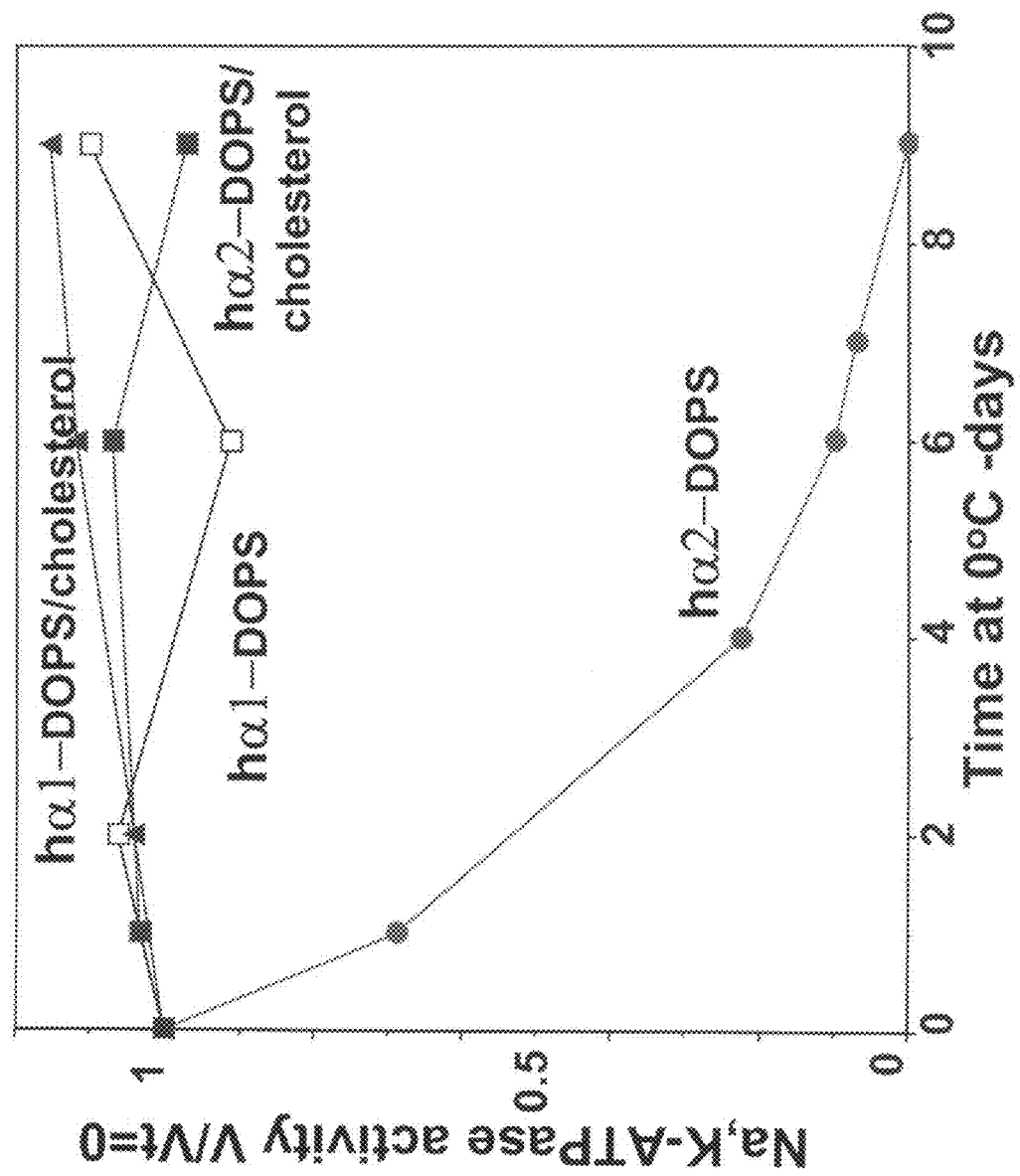

FIG. 11 is a graph illustrating the stabilization of $\alpha_2\beta_1$ by cholesterol DOPS at 0° C.

Figure 12:
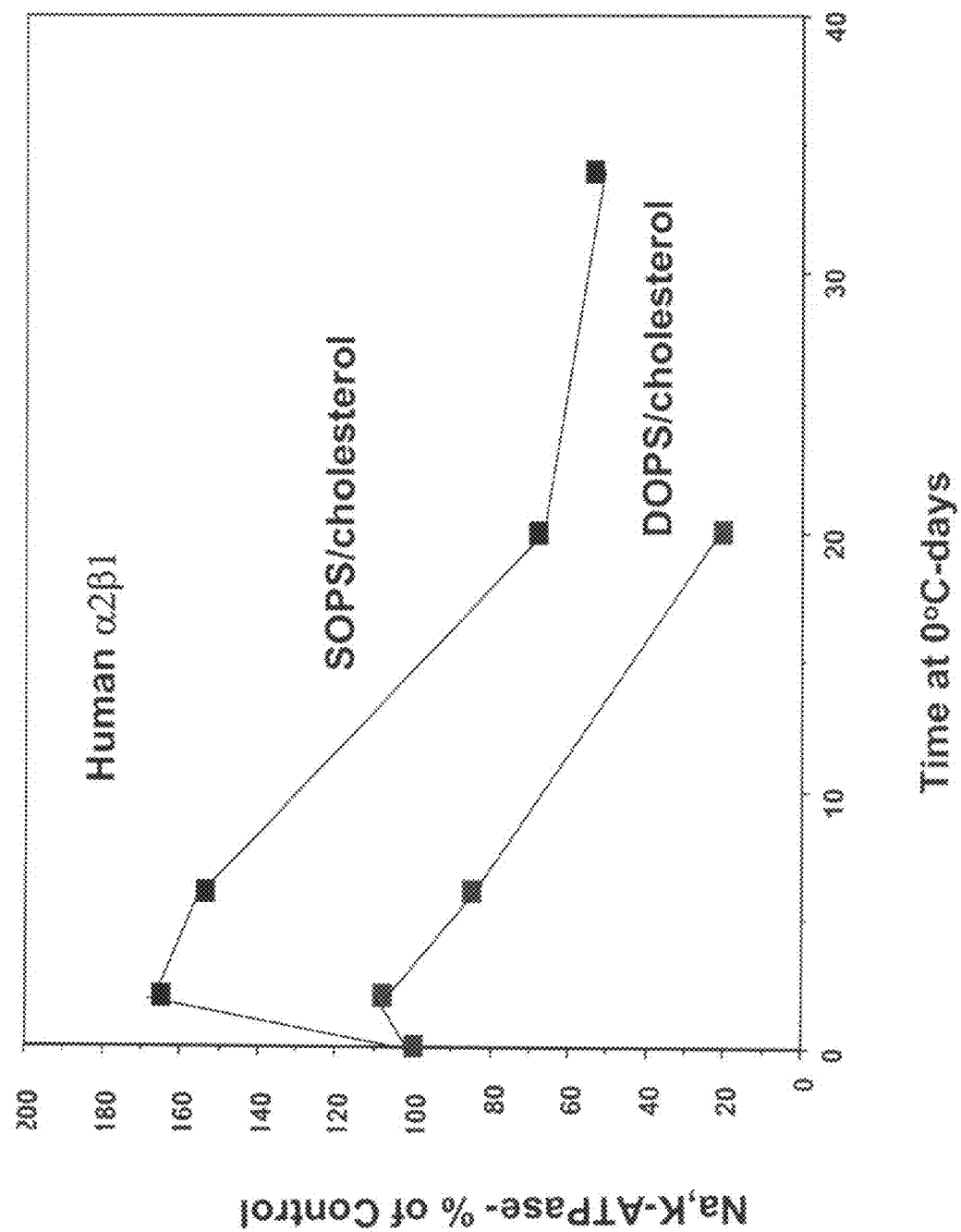

FIG. 12 is a graph illustrating the superiority of cholesterol SOPS over cholesterol DOPS at stabilizing $\alpha_2\beta_1$ at 0° C.

Figure 13:
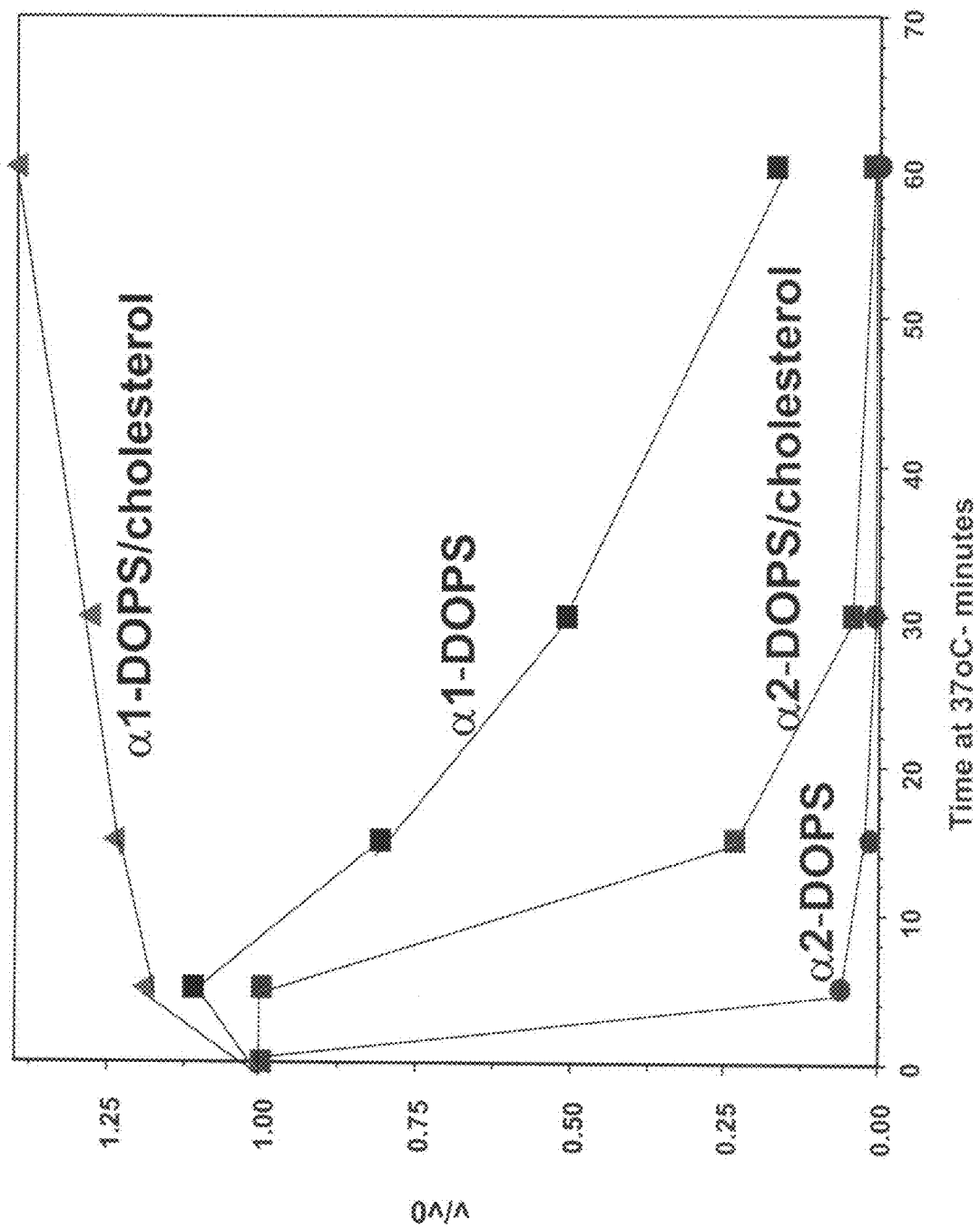

FIG. 13 is a graph comparing the stability of $\alpha_2\beta_1$ and $\alpha_1\beta_1$ at 37° C.

Figure 14:
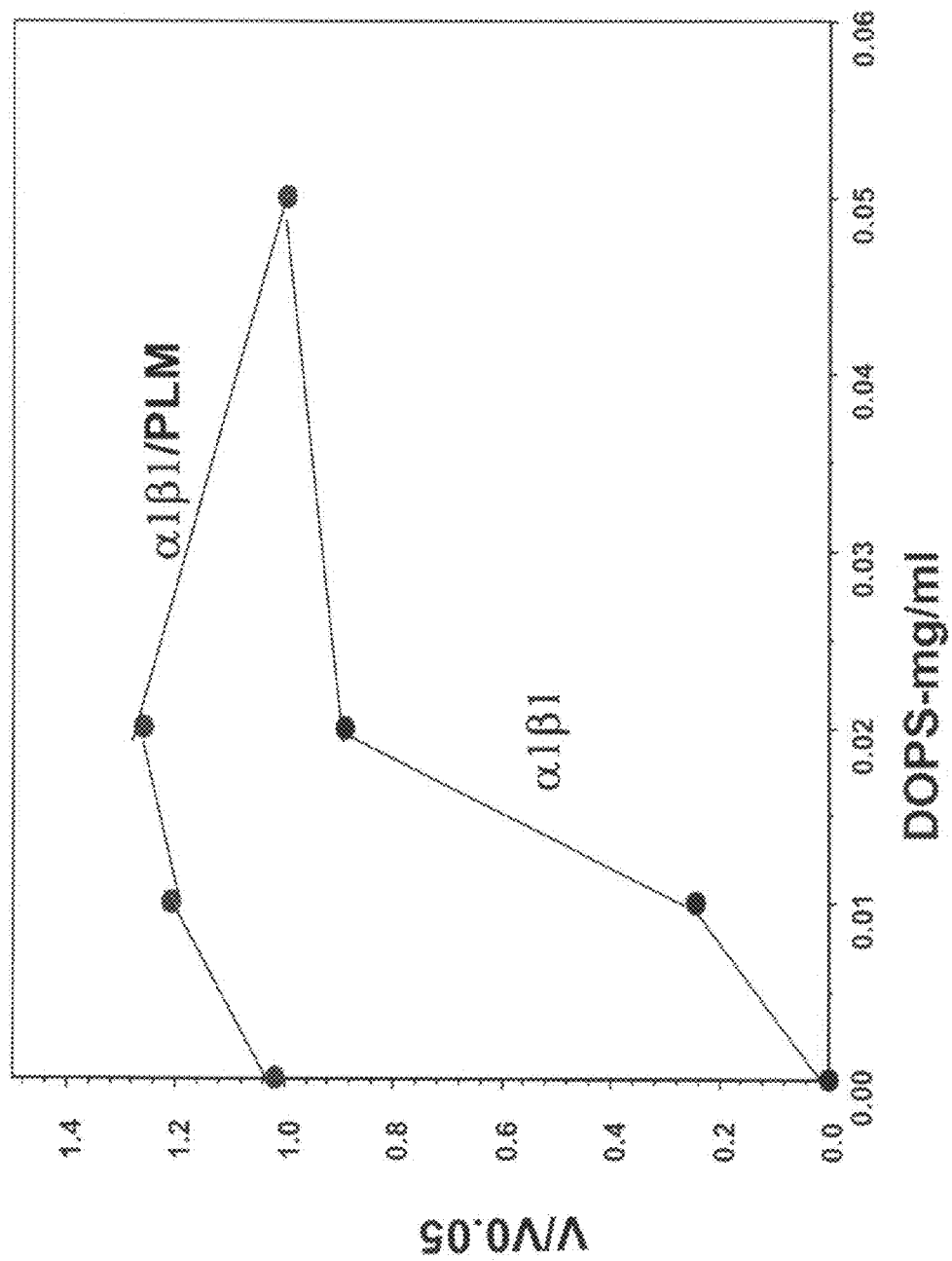

FIG. 14 is a graph illustrating the stabilizing effect of FXYD1 (PLM) on $\alpha_1\beta_1$. Addition of DOPS is not necessary in the presence of FXYD1.

FIGS. 15A-B are graphs illustrating the stabilization of $\alpha_1\beta_1$ against thermal inactivation by FXYD1.

Figure 16:
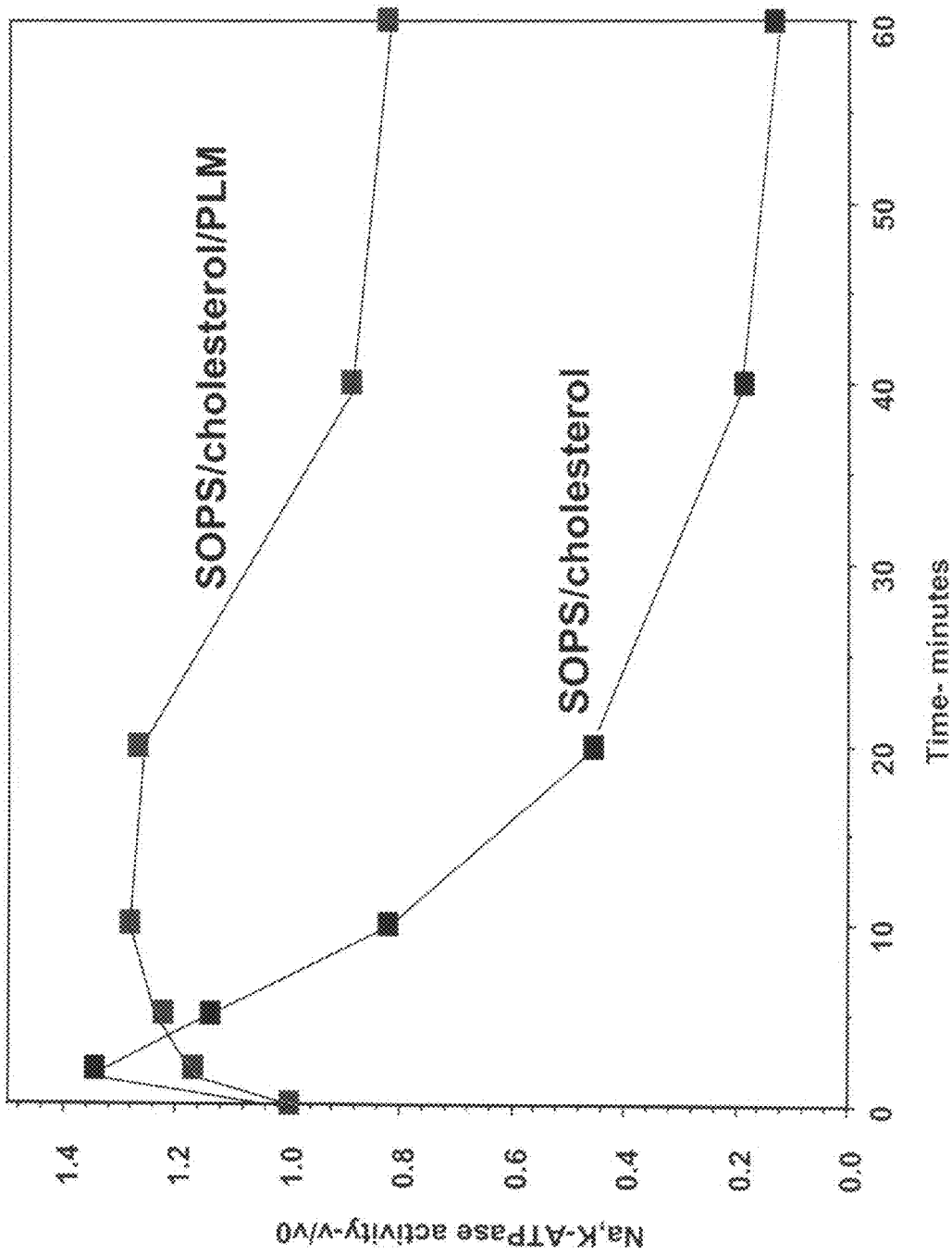

FIG. 16 is a graph illustrating the stabilization of $\alpha_2\beta_1$ against thermal inactivation by FXYD1.

FIGS. 17A-B are graphs illustrating the inhibition of $\alpha_2\beta_1$ and $\alpha_1\beta_1$ by ouabain 10 minutes following administration (FIG. 17A) and 60 minutes following administration (FIG. 17B)

FIGS. 18A-B are graphs illustrating the inhibition of $\alpha_2\beta_1$ and $\alpha_1\beta_1$ by digoxin (FIG. 18A) and neriifolin (FIG. 18B).

DESCRIPTION OF THE PREFERRED EMBODIMENTS

The present invention is of purified Na,K-ATPase and methods of obtaining same. Specifically, the present invention can be used to identify agents that are capable of regulating an activity of Na,K-ATPase.

The principles and operation of the purified Na,K-ATPases according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Cardiac glycosides (CG) such as digoxin, are widely used in clinical practice, for the treatment of congestive heart failure. However, digoxin has a narrow therapeutic window (particularly in K-depleted patients) and has been shown to induce cardiac arrhythmias. Cardiac glycosides exert their positive inotropic effects by inhibiting cardiac Na,K-ATPase. This proteinaceous pump consists of both α and β subunits. In humans, three isoforms of the pump complex exist—$\alpha_1\beta_1$ $\alpha_2\beta_1$ and $\alpha_3\beta_1$.

It is believed that CG toxicity results from excessive inhibition of Na,K-ATPase, which ultimately induces arrhythmias. Since the α1 isoform is the major form in human heart, while α2 (and α3) are present at lower levels, excessive inhibition is inevitably associated with the housekeeping α1 isoform. Therefore, by avoiding inhibition of α1, and restricting inhibition to a minor fraction of the Na,K-ATPase molecules, excess inhibition of Na,K-ATPase should be automatically avoided. Thus, in principle, either a α2 or a α3-specific inhibitor should be a safer inotropic drug.

Testing selectivity of novel inhibitors with human heart muscle itself is impractical because the tissue contains all three isoforms and is not readily available. Therefore, identification of specific inhibitors requires large quantities of purified isoforms of Na,K-ATPase.

Human isoforms of Na,K-ATPase have been expressed in yeast *S. Cerevesiae* cells (Muller-Ehmsen et al., American J. Physiol Cell Physiol, 281: c1355-C1364, 2001). However, the *S. Cerevesiae* expression system does not provide enough material for large scale screening of inhibitors since the density of the expressed Na,K-ATPases was not sufficiently high for purification and thus the induced proteins were unstable (α2).

Human isoforms of Na,K-ATPase have also been expressed in *Xenopus* oocytes. However, electrophysiological measurements thereof were shown to be too unwieldy for large scale screening (Crambert et al 2000, J Biol Chem, 275, 1976-1986; Crambert et al, 2004, Mol Pharmacol, 65, 335-341).

The present inventors have previously expressed porcine Na,K-ATPase in the methanotrophic yeast *P. pastoris* (Cohen et al., 2005, J Biol Chem, 280, 16610-16618). The present inventors showed that following expression of Porcine α/his$_{10}$-β subunits and solubilization of the yeast membranes in n-dodecyl-β-maltoside (DDM), detergent-soluble α/his$_{10}$-β complexes could be purified utilizing a combination of Ni2+-NTA bead chromatography and size-exclusion HPLC. The procedure produced 70-80% pure porcine Na,K-ATPase. This complex, two-step procedure however is not applicable for producing large quantities of Na,K-ATPase for high through-put screening.

Whilst reducing the present invention to practice, the present inventors have discovered that affinity purification of a homogenate of *P. pastoris* Na,K-ATPase expressing cells comprising a low concentration of EDTA on a $Co^{2+}$-chelate affinity resin greatly enhanced the purification of the Na,K-ATPase (FIG. 1A). This novel method of purification generated 80-90% pure Na,K-ATPase. By abolishing the HPLC step, the present purification method is far more suitable for generating large amounts of active Na,K-ATPase for high throughput screening.

Figure 2:
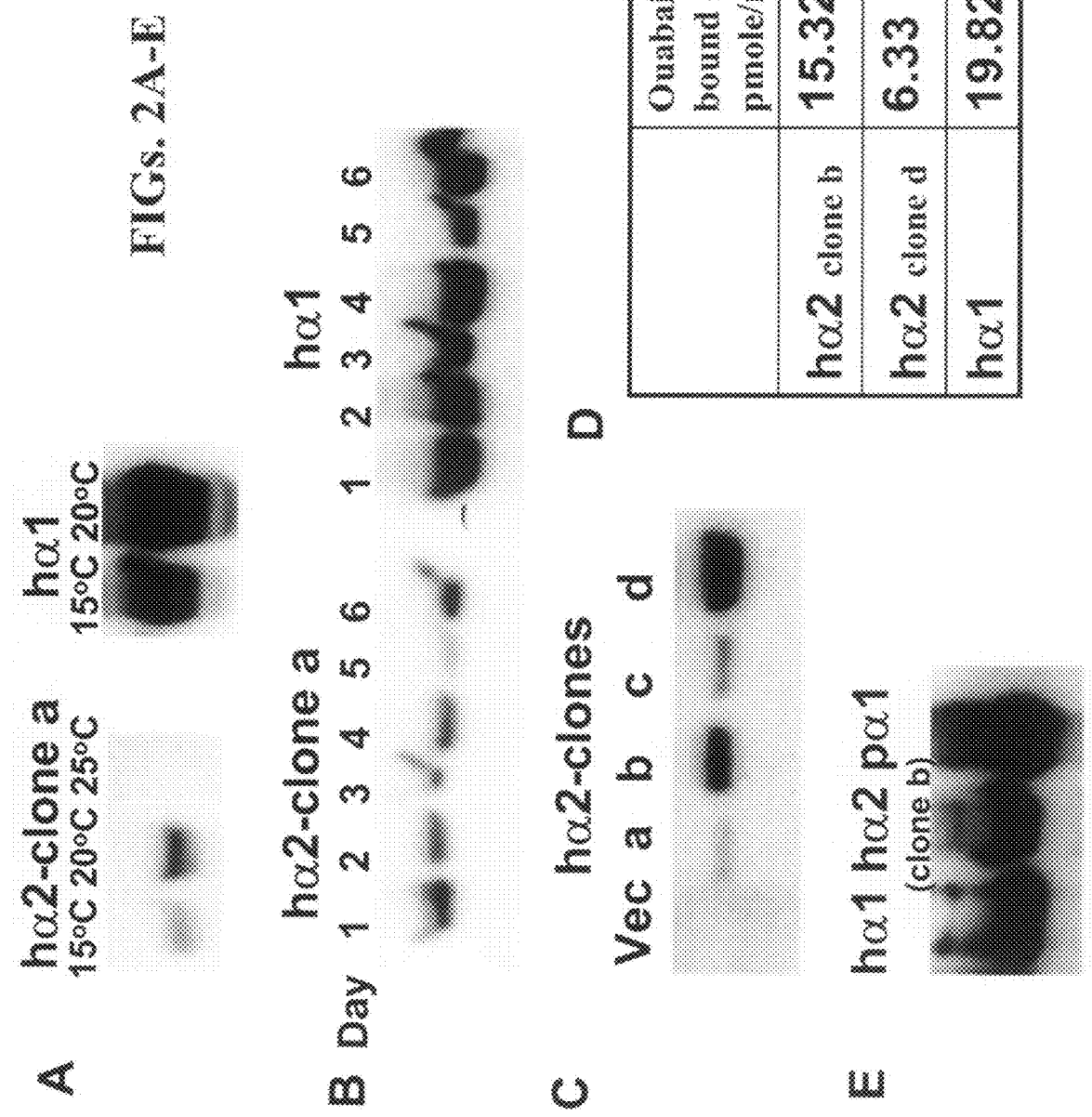

In addition, the present inventors have uncovered that growth of *P. pastoris* at 20° C. greatly enhanced the expression of the $\alpha_2\beta_1$ isoform and allowed generation of clones with a high copy number of incorporated $\alpha_2$ and $\beta_1$ genes (FIG. 2A and FIG. 4B).

Whilst further reducing the present invention to practice the present inventors have shown (FIGS. 7 and 8) that that the stability of the purified proteins over time may be enhanced by washing and eluting same with phosphatidyl serines containing one unsaturated (sn2 position) and one saturated (sn1) fatty acid side chain (e.g. SOPS, POPS and DOPS). The stability of the purified proteins was further enhanced by including cholesterol in the washing and elution medium (FIGS. 9A-C, 10, 11, 12 and 13).

In addition, the present inventors have shown that purification of Na,K-ATPase in the presence of FXYD polypeptides also enhances stabilization thereof (FIGS. 14, 15A-B and 16). This stabilization was shown to be independent of the inclusion of either phospholipids and/or cholesterol in the purification procedure.

Thus, according to one aspect of the present invention, there is provided a method of purifying a Na,K-ATPase, the method comprising:

(a) contacting a yeast membrane preparation comprising the Na,K-ATPase with a divalent metal chelator; and (b) affinity purifying the Na,K-ATPase from the yeast membrane preparation, thereby purifying the Na,K-ATPase.

As used herein, the term "purifying" refers to a method of at least partially isolating the Na,K-ATPase from other membrane proteins.

The term "Na,K-ATPase", as used herein, refers to at least an active portion of the membrane protein Na,K-ATPase (i.e., a portion having Na,K-ATPase catalytic activity)—EC 3.6.3.9.

As used herein the phrase "Na,K-ATPase activity" refers to the catalytic activity of Na,K-ATPase rendering the protein capable of transporting sodium and potassium ions across a cell membrane.

Na,K-ATPase comprises two subunits ($\alpha$ and $\beta$), both of which are encoded by multigene families. Thus, the Na,K-ATPase of the present invention may comprise any combination of one of the four isoforms of $\alpha$ ($\alpha_1$, $\alpha_2$, $\alpha_3$ and $\alpha_4$) and one of the three isoforms of $\beta$ ($\beta_1$, $\beta_2$ and $\beta_3$). Preferably, the Na,K-ATPase comprises combinations of subunits that are present in the human heart—i.e. $\alpha_1,\beta_1$ $\alpha_2,\beta_1$ and $\alpha_3\beta_1$. Thus, for example the Na,K-ATPases may comprise amino acid sequences that are at least 80%, more preferably at least 90% and most preferably 100% homologous to that encoding human $\alpha_1$ (Swiss Prot No. P05023), porcine $\beta_1$ (Swiss Prot No. P05027) Na,K-ATPase; human $\alpha_2$ (Swiss Prot No. P50993, porcine $\beta_1$ Na,K-ATPase; and porcine $\alpha_1$ (Swiss Prot No. P05024), porcine $\beta_1$ Na,K-ATPase.

In addition, the Na,K-ATPase of the present invention may comprise conservative variations of the subunit amino acid sequences described herein above.

The phrase "conservative variation" as used herein refers to the replacement of an amino acid residue by another, biologically similar residue. Examples of conservative variations include the substitution of one hydrophobic residue such as isoleucine, valine, leucine, or methionine for another, or the substitution of one solar residue for another, such as the substitution of arginine for lysine, glutamic acid for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Membrane preparations of the present invention may be derived from yeast cells expressing exogenous Na,K-ATPase.

To generate such yeast membrane preparations, polynucleotides comprising nucleic acid sequence encoding Na,K-ATPase subunits may be used to transform yeast cells.

The term "nucleic acid sequence" refers to a deoxyribonucleic acid sequence composed of naturally-occurring bases, sugars and covalent internucleoside linkages (e.g., backbone) as well as oligonucleotides having non-naturally-occurring portions which function similarly to respective naturally-occurring portions. Such modifications are enabled by the present invention provided that recombinant expression is still allowed.

A nucleic acid sequence encoding Na,K-ATPase according to this aspect of the present invention can be a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing there between. The intronic sequences can be of any source, including of other genes, and typically will include conserved splicing signal sequences. Such intronic sequences may further include cis acting expression regulatory elements.

Preferably, the Na,K-ATPase subunits are encoded by polynucleotide sequences that are present in humans as this is important for drug testing. It will be appreciated that the present invention also contemplates Na,K-ATPase subunits that are encoded by polynucleotide sequences that are present in other mammals such as pigs.

Thus, exemplary polynucleotide sequences that may be used to encode the Na,K-ATPases of the present invention are presented in Table 1 hereinbelow:

TABLE 1

| Subunit | Genbank accession number |
| --- | --- |
| Human $\alpha_1$ | X04297 |
| Human $\alpha_2$ | NM_000702 |
| Human $\alpha_3$ | NM_152296 |
| Human $\beta_1$ | NM_001677 |
| Porcine $\beta_1$ | X04635 |
| Porcine $\alpha_1$ | X03938 |

In order to obtain yeast membrane preparations that comprise Na,K-ATPase, the polynucleotides encoding same are ligated into nucleic acid expression vectors, such that the polynucleotide sequence is under the transcriptional control of a cis-regulatory sequence (e.g., promoter sequence). Preferably the polynucleotide sequences encoding both subunits are ligated into the same expression vector to ensure correct stroichiometry.

This may be achieved by the inclusion of an internal ribosome entry site (IRES) and sequences for genomic integration of the promoter-chimeric polypeptide, as further described hereinbelow.

A number of vectors containing constitutive or inducible promoters can be used for transforming yeast cells. For a review, see Current Protocols in Molecular Biology, Vol. 2, 1988, ed. Ausubel et al., Greene Publish. Assoc. & Wiley Interscience, ch. 13; Grant et al., 1987, "Expression and Secretion Vectors for Yeast," in Methods in Enzymol. 153: 516-544; Glover, 1986, DNA Cloning, Vol. II, IRL Press, Wash., D.C., Ch. 3; and Bitter, 1987, "Heterologous Gene Expression in Yeast," in Methods in Enzymol. 152:673-684. A constitutive yeast promoter such as ADH or Leu2 or an inducible promoter such as GAL can be used ("Cloning in Yeast," ch. 3, R. Rothstein In: DNA Cloning, Vol. II, A Practical Approach, Ed. D. M. Glover, 1986, IRL Press, Wash. D.C.). Alternatively, vectors can be used which promote integration of foreign DNA sequences into the yeast chromosome.

The vector typically includes at least one selectable marker, such that clones expressing the Na,K-ATPase can be suitably selected. For example, selection of positive clones in SMD1165, a protease deficient strain (his4, prb1) of *P. pastoris* may be effected by selection for His+, Mut$^S$ (methanol utilization slow) transformants (see Materials and Methods of the Examples section herein below and Strugatsky et al., 2003, J Biol Chem, 278, 46064-46073).

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Thus for example, the Na,K-ATPases of the present invention are typically expressed with affinity tags in order to aid in their subsequent purification. Examples of affinity tags include, but are not limited to a polyhistidine-tag, a polyarginine-tag, a FLAG-tag, a Strep-tag, a c-myc-tag, a S-tag, a calmodulin-binding peptide, a cellulose-binding peptide, a chitin-binding domain, a glutathione S-transferase-tag, and a maltose binding protein. According to a preferred embodiment of this aspect of the present invention, the Na,K-ATPases are expressed with polyhistidine tags.

Any strain of yeast may be used to express the Na,K-ATPase so long as it does not comprise factors which inhibit its expression and allows appropriate post-translational modifications (e.g. glycosylation) thereto. Examples of yeast species which may be used according to this aspect of the present invention include *S. Cerevesiae* and *P. Pastoris*. Preferably, the Na,K-ATPase is expressed in *P. Pastoris* since this yeast species provides a very high yield of membrane protein.

Induction of expression of the transfectants may be effected in various ways depending on the expression vector used and the yeast species that was transformed. As described in the Examples section below, *P. pastoris* yeast cells may be induced to express the Na,K-ATPase by addition of methanol (e.g. 0.5% methanol may be added daily for 5 days). During the induction phase, the yeast cells are typically grown at a temperature less than 30° C. Preferably, the temperature is between 20-30° C. Each Na,K-ATPase isoform may require a particular temperature for optimal expression. For example, the present inventors have shown that optimization of expression of the $\alpha_2$ Na,K-ATPase isoform requires growth at 20° C.—see FIG. 2A. Determining the optimal temperature is well within the scope of one skilled in the art.

Optimization of expression may also be effected by screening a large number (e.g. 50) Mut$^S$ clones and selecting the clone with the highest copy number of transfectants. The present inventors have previously shown that there was a large variability in expression of the α subunit in different Mut$^S$ clones, and that the highest level of expression reflects the highest copy number of the incorporated α and β genes (Strugatsky et al., 2003, J Biol Chem, 278, 46064-46073). Screening may be affected by many different methods known in the art e.g. by dot blot analysis.

Following selection of positive colonies, yeast cells may be inoculated with the positive colonies in order to generate greater quantities of the Na,K-ATPase. Methods for growing and inoculating yeast cultures are well known in the art. Transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a yeast cell is cultured to produce the recombinant polypeptide of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes and petri plates. Culturing can be carried out at a temperature, pH and oxygen content appropriate for a recombinant cell. Such culturing conditions are within the expertise of one of ordinary skill in the art.

Yeast cells transformed according to the teachings described hereinabove contain membranes comprising a high density of Na,K-ATPases. Thus, according to another aspect of the present invention, there is provided an isolated cell expressing exogenous Na,K-ATPase, wherein at least one of said subunits is of human origin and wherein a ouabain binding capacity of the cell is at least 15 pmoles ouabain binding capacity per mg of membrane protein. This corresponds to approximately 0.5-2 pmoles/10$^9$ cells at the surface (Strugtasly et al, 2003).

Methods of measuring ouabain binding capacity are known in the art and further described in the Examples section hereinbelow.

Cell membranes may be prepared from the yeast cells using methods known in the art. An exemplary method for preparing membranes from *P. pastoris* cells is described by Strugatsky et al (Strugatsky et al., 2003, J Biol Chem, 278, 46064-46073). In short, pelleted cells are resuspended in a buffer comprising protease inhibitors and mixed with an equal volume of glass beads (0.5 mm) and disrupted using a Glass Bead Beater (e.g. Biospec Products, Inc.). Unbroken cells and heavy membranes are removed by centrifugation at 10,000×g for 10 min and light membranes are collected at 100,000×g for 1 h. The pellet is suspended in buffer comprising protease inhibitors (as above).

The generated membrane preparation may be frozen (e.g. at −80° C.) and stored until required. Crude membrane preparations also be further refined prior to the affinity purification in order to increase the level of purification. Any method of refinement is envisaged by the present inventors as long as it does not affect the activity of the Na,K-ATPase. For example, the membrane preparation may be treated with urea e.g. (e.g. 2 M) and 100 mM KCl prior to the final high speed centrifugation, as described in the Examples section below. This urea wash removes about 50% of the membrane-associated protein without affecting the Na,K-ATPase activity.

Another method envisaged by the present inventors for refining crude cell membrane preparations is by sonication, see e.g. Maris G. N. Hartmanis, Thressa C. Stadtman, PNAS, Vol. 84, No. 1 (Jan. 1, 1987), pp. 76-79.

As mentioned above, in order to further purify the Na,K-ATPases expressed in the yeast cells the cell membrane preparations are contacted with a divalent cation chelator prior to affinity purification.

Exemplary divalent cation chelators include but are not limited to EDTA, EGTA and CDTA. Preferably, the divalent cation chelator is EDTA.

The present inventors have shown that low concentrations of EDTA in the incubation medium reduce binding of contaminant proteins to the affinity beads and improve purity. EDTA is preferably added at an amount less than 100 μM per mg/ml of protein and greater than 10 μM per mg/ml of protein. The EDTA must be titrated carefully, for excessively high concentrations (100 μM) remove Co from the beads and no protein is eluted (FIG. 1A, lane 4). An optimal concentration of EDTA is about 50 μM per mg/ml.

Preferably, the divalent cation chelator is added to a homogenate of the cell membrane preparation. An exemplary method for preparing a homogenate of *P. pastoris* expressing cells is described hereinbelow.

Urea-treated membranes (as described hereinabove) are homogenized with n-dodecyl-β-maltoside (DDM:protein, 2:1 w/w) (cat. No D310, Anatrace) in a medium containing NaCl, 250 mM; Tris.HCl, 20 mM pH 7.4; imidazole, 5 mM; PMSF, 0.5 mM; and glycerol, 10%. The protein concentration can be varied from 1-5 mg/ml and DDM adjusted accordingly from 2-10 mg/ml respectively. The unsolubilized material is removed by ultracentrifugation.

According to this aspect of the present invention, the Na,K-ATPase is affinity purified following addition of EDTA. The method of affinity purification is dependent on the affinity tag which is expressed on the Na,K-ATPase. Thus, for example if the Na,K-ATPase comprises a histidine affinity tag, it may be affinity purified using a $Co^{2+}$-chelate affinity resin or a $Ni^{2+}$-NTA affinity resin. Preferably, the affinity resin is $Co^{2+}$-chelate as this has been shown to produce a higher level of purification of the Na,K-ATPase.

Following binding of the Na,K-ATPase to the affinity resin, the affinity resin is optionally washed to remove any contaminants that have not bound specifically to the resin. The wash solution typically comprises components that are tailored to the specific affinity resin. Thus, for example a wash solution that may be used to release any non-specific polypeptides that have bound to the $Co^{2+}$ affinity resin may comprise a non-ionic detergent (e.g. DDM or C12E8) and a low concentration of imidazole (e.g. 10 mM). At such concentrations, Imidazole binds to the $Co^{2+}$ affinity resin, and removes non-specifically bound contaminants. An exemplary wash solution is described in the Examples section hereinbelow.

Following washing of the affinity resin, the Na,K-ATPase may optionally be eluted from the affinity resin. Similarly to the wash solution, the eluting solution is also specifically tailored to the affinity resin being used. Accordingly, an eluting solution that may be used to elute Na,K-ATPase from a $Co^{2+}$ affinity resin may comprise a non-ionic detergent (as described hereinabove) and a higher concentration of imidazole (e.g. 150 mM). At such concentrations, Imidazole competes with the his-tagged Na,K-ATPase and releases it from the resin. An exemplary eluting solution is described in the Examples section hereinbelow.

Preferably both the wash and eluting solution comprise both glycerol (e.g. 10%) as this component comprises a general protein stabilizing activity and protease inhibitors.

Preferably, the washing and eluting are effected at 0° C. so that the Na, K-ATPase retains as much activity as possible.

The present inventors have previously shown that for the Na,K-ATPase to be functional, the Na,K-ATPase should be in contact with phospholipids. Accordingly, it is preferable that both the wash solution and the eluting solution comprise phospholipids. Exemplary phospholipids that may be used according to this aspect of the present invention include, but are not limited to DOPS, SOPS, POPS, DMPS, DPPS, DOPC, DOPI, and DSPS. Preferably, the phospholipids are present at about 0.05 mg/ml.

The present inventors have also shown that for the Na,K-ATPase to maintain activity over a length of time, it is preferable that the phospholipids in the wash and eluting solution are acid phospholipids. Preferably such acid phospholipids comprise phosphatidyl serines containing one unsaturated (sn2) and one saturated (sn1) fatty acid side chain since these were shown to have the greatest effect at increasing stability over time. Accordingly, particularly preferred phospholipids in the wash and eluting solution are SOPS, DOPS and POPS and most preferred phospholipids are SOPS. Synthetic lipids may be obtained commercially e.g. from Avanti.

In addition, the present inventors have shown that incorporating cholesterol in the wash and eluting solutions further enhances the stability of the Na,K-ATPase over time. An exemplary concentration of cholesterol is about 0.01 mg/ml.

The present inventors have further shown that binding a yeast membrane preparation comprising the Na,K-ATPase with an FXYD polypeptide also enhances the stability of the purified Na,K-ATPase. This stabilizing effect was shown to be independent of the stabilizing effect of phospholipids alone or in conjunction with cholesterol/

As used herein the phrase "FXYD polypeptide" refers to at least an active portion of the membrane protein FXYD (i.e., a portion having FXYD activity).

As used herein the phrase "FXYD activity" refers to the ability to modulate the function of Na, K-ATPase.

The FXYD polypeptide may be any one of the six FXYD polypeptides known to interact with Na, K-ATPase and affect its kinetic properties in specific ways. According to a presently preferred embodiment of the present invention the FXYD polypeptide is FXYD1, also known as phospholemann or PLM (Genbank Accession No. H23593).

The FXYD polypeptide may be co-expressed with the Na,K-ATPases or may be expressed in an independent expression vector. Any suitable cell may be used to express the FXYD polypeptide, for example a yeast cell, a mammalian cell, a plant cell, an insect cell or a bacterial cell. Preferably the cell is a yeast cell so that amounts of FXYD polypeptides roughly correspond to the amounts of the expressed Na, K-ATPases.

FXYD polypeptides expressed independently of Na, K-ATPases in yeast cell membranes are preferably solubilized in detergent (e.g. in DDM) and subsequently contacted with the yeast cell membranes expressing the Na, K-ATPase. The FXYD polypeptides may be incubated with the Na, K-ATPases prior to binding to the affinity column or following binding to the affinity column. Preferably the FXYD polypeptides are incubated with the Na, K-ATPases for a sufficient length of time to allow binding of the two polypeptides prior to elution from the affinity columns (e.g. 24 hours at 4° C.). Following elution the Na,K-ATPases may be deglycosylated by such enzymes as ENDO-H.

The Na,K-ATPases purified according to the teachings described hereinabove are typically 85-90% or preferably 85-95% pure. Methods of determining the level of purity of the Na,K-ATPase are well known in the art. For example, following purification the Na,K-ATPase may be run on an SDS PAGE gel. The gel may be subsequently stained for proteins (e.g. coomassie or silver staining) and the strength of the band corresponding to Na,K-ATPase may be compared to the strength of all the other non-related protein bands in the same lane by densitometry scanning.

The Na,K-ATPases purified according to the teachings described hereinabove are highly stable. It has been shown that the half-life thereof for loss of activity at 0° C. is at least 15 days and may reach as long as long as 20 days or more. Na, K-ATPases purified in the presence of FXYD1 are also highly stable (see FIGS. 15A-B and FIG. 16). Specifically, SOPS/cholesterol/FXYD1 Na,K-ATPase complexes were shown to be stable at 45° C. for over three hours.

Methods of measuring Na,K-ATPase activity are known in the art. An exemplary method is further described in the Examples section hereinbelow.

The purified Na,K-ATPases of the present invention may be used to identify agents (e.g. cardiac glycosides) capable of specifically regulating (e.g. stabilizing) an activity of a particular isoform of Na,K-ATPase. As mentioned in the Background section hereinabove, it has been proposed that cardiac glycoside toxicity may result from excessive inhibition of Na,K-ATPase. Therefore identifying agents that are capable of targeting isoforms of Na,K-ATPase which are present at lower levels than the housekeeping α1 isoform may allow for safer therapeutic cardiac glycosides.

The method according to this aspect of the present invention is effected by determining an activity of the purified Na,K-ATPase in the presence and absence of the candidate agent. An agent which promotes inhibition of a particular isoform of Na,K-ATPase (e.g. α2 isoform) may be selected as a possible therapeutic.

In addition, since cardiac glycosides dissociate slowly from the Na,K-ATPase, the effect of toxic concentrations is not readily reversed. Identification of agents with dissociate in a faster fashion from the Na,K-ATPase, either for both isoforms, or in an isoform-specific way, could also be important in the search for a safer CG.

Methods of measuring the dissociation of cardiac glycosides from Na,K-ATPase are known in the art. For example, $^3$H-ouabain binding assays may serve for characterization of such binding properties.

An important aspect of CG function concerns endogenous CG's which have been isolated from brain, blood plasma, adrenal glands and other tissues. Several types of cardiac glycosides have been isolated including ouabain (EO) or an isomer, which are cardenolides with a five-membered lactone ring, and bufadienolides such as marinobufogenin with a six-membered lactone ring. EO is synthesized in the adrenal cortex and brain and is involved in regulation of blood pressure and cardiac hypertrophy. The evidence for EO has lead to design of antagonists, which act as anti-hypertensive drugs (Ferrari et al., 2006, Am J Physiol Regul Integr Comp Physiol, 290, R529-535; Ferrari et al., 1998, J Pharmacol Exp Ther, 285, 83-94). The purified Na,K-ATPases of the present invention would aid in the designing of such antagonists and in particular the designing and screening of antagonists selective for a particular Na,K-ATPase isoform.

In brain the $\alpha_1$ isoform is ubiquitous, while the $\alpha_3$ isoform is expressed heavily in neurons, and the $\alpha_2$ is expressed strongly in glial cells (Specht and Sweadner, 1984, Proc Natl Acad Sci USA, 81, 1234-1238; Sweadner, 1979, J Biol Chem, 254, 6060-6067; Sweadner, 1989, Biochim Biophys Acta, 988, 185-220), although it is also clear that the expression patterns are complex and cannot be characterized simply in terms of neuronal ($\alpha_1$, $\alpha_3$) and glial ($\alpha_1$, $\alpha_2$) isoforms. Thus, identifying agents that are specific for the $\alpha_1$ and/or $\alpha_3$ may find use in neuroprotection against ischemic stroke. Following identification of promising agents according to the method of this aspect of the present invention, subsequent characterization of the agent(s) may be performed at the molecular, cellular, organ (heart) and whole body levels.

The present inventors have successfully purified α/β/FXYD complexes. Since FXYDs are major regulator of Na,K-ATPase in the heart and skeletal muscle, such purified complexes may be used to look for possible differences in inhibitor specificity of isoforms with and without FXYD.

In principle, if an inhibitor affected αβ-FXYD interactions (i.e either strengthening or weakening them), one could observe a different effect of inhibitor in the absence or presence of FXYD and a different selectivity pattern for α1β1 or α2β1 isoform in the absence or presence of FXYD. An inhibitor that disrupted αβ-FXYD interactions could have effects similar to the effects of β-adrenergic agents, which induce phosphorylation of the FXYD and cause cardiac myocytes to pump out Na more quickly. In the intact cardiac muscle this type of effect is predicted to bring about a more rapid relaxation after contraction (lusitropic effect) and should be beneficial for cardiac contraction (Bers, 2002, Nature, 415, 198-205).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Media

YPD: (1% Bacto yeast extract, 2% bacto-peptone, 2% dextrose, to solidify the medium 2% Bacto-agar were added).

YNB: (1.34% yeast nitrogen base without amino acids, 0.04% biotin, 1% glycerol).

BMG: (1.34% yeast nitrogen base without amino acids, 0.04% biotin, 0.1M potassium phosphate buffer pH 6.0; glycerol 1-3%).

BMM: (1.34% yeast nitrogen base without amino acids, 0.04% biotin, 0.5% methanol, 0.1M potassium phosphate buffer pH 6.0).

Basal salt medium: (per liter) 26.7 ml $H_3PO_4$, 0.93 $gCaSO_4.2H_2O$, 18.2 g $K_2SO_4$, 14.9 g $MgSO_4.7H_2O$, 4.13 g KOH, 40 g glycerol.

Trace element solution: PMT1 (per liter): 6.0 g $CuSO_4.5H_2O$, 0.8 g, KI, 3.0 g $MnSO_4.H_2O$, 0.2 g $Na_2MoO.2H_2O$, 0.2 g $H_3BO_3$, 0.5 g $CaSO_4.2H_2O$, 20 g $ZnCl_2$, 65 g $FeSO_4.7H_2O$, 0.2 g Biotin, 1 ml conc. $H_2SO_4$. Filter-sterilized and add 2 ml/L of basal salts medium. The trace salt solution is also added to the methanol feed supply at 2 ml/L.

Construction of the Clones pHIL-D2 (Porcine $\alpha 1/His_{10}\beta 1$; Human $\alpha 1$/Porcine $His_{10}\beta 1$; Human $\alpha 2$/Porcine $His_{10}\beta 1$; and pHIL-D2(FXYD1-PLM)

A pHIL-D2 vector (Invitrogen) construct containing cDNAs encoding porcine $\alpha 1$ (Accession X03938) and porcine $\beta 1$ (Accession no. X04635) with a 10× histidine tag at its N' terminus ($\alpha 1/His_{10}\beta 1$) has been described previously (Cohen et al., 2005, J Biol Chem, 280, 16610-16618). Human $\alpha 1$ (Accession X04297) in vector pNKS2, and human $\alpha 2$ (Accession NM_000702) in vector pSD5 were a gift from K. Geering Univ. Lausanne, Switzerland. The coding regions were excised with XbaI and subcloned into the pHIL-D2-(porcine $\alpha 1/His_{10}\beta$ thus replacing the porcine $\alpha 1$ insert. Human FXYD1 (PLM-Accession H23593) was subcloned into the EcoRI site of pHIL-D2 (Lifshitz et al., 2006, J. Biol. Chem., 281, 15790-15799).

Yeast Transformation Selection and Growth

SMD1165, a protease deficient strain (his4, prb1) of *P. pastoris* was transformed with 10 µg of NotI linearized pHIL-D2(p$\alpha 1$/pHis$_{10}$-$\beta 1$; h$\alpha 1$/pHis$_{10}$-$\beta 1$; h$\alpha 2$/pHis$_{10}$-$\beta 1$) construct. Preparation of spheroplasts and selection for His+, Mut$^S$ transformants was done as described (Cohen et al., 2005, J Biol Chem, 280, 16610-16618; Strugatsky et al., 2003, J Biol Chem, 278, 46064-46073). Dot blot analysis was used to scan for maximal copy number of the incorporated $\alpha$ and $\beta$ genes as described in Strugatsky et al., (Strugatsky et al., 2003, J Biol Chem, 278, 46064-46073). Dot blot analysis has also been used to scan for maximal copy number of integrated PLM, as described in (Lifshitz et al., 2006, J. Biol. Chem., 281, 15790-15799). A radioactive probe was synthesized from PLM cDNA using a random prime labeling kit (rediprime, Amersham cat. No RPN 1633). Linear cDNA of PLM in pHIL-D2 (without $\alpha$ and His$_{10}$-$\beta$ cDNA) was used to transform spheroplasts, in a similar way as the pHIL-D2($\alpha$/His$_{10}$-$\beta$ vector. This clone was used to express PLM alone and reconstitute it in vitro with the $\alpha$/his$_{10}$-$\beta$ complex.

Cell Growth and Induction of Protein Synthesis

Routinely, yeast cultures were propagated in YPD medium. To induce expression of the recombinant Na, K-ATPase, 5 ml of BMG liquid medium was inoculated with a single colony and incubated O/N with vigorous shaking at 30° C. or 25° C. "Log phase mode of induction": The over-night culture was further diluted by thousand fold to its final volume and continued to grow for the next 20-26 hours up to an $OD_{600}$~2-4. After the culture reached the desired OD, cells were collected by centrifugation at 3000 g for 10 minutes at RT and re-suspended in fresh BMM medium for the methanol induction phase. The methanol induction period was 5 days. 0.5% methanol was added daily. After the induction period, cells were collected and stored at –20° C. or used immediately for membrane preparations.

Growth in Spinner Flasks and Bioreactor

Initially, upscaling of yeast production was performed in an 8 L Bellco Spinner Flask™ and a magnetic stirrer. The air was supplied from a compressed dry air balloon via a flow meter and 0.2 µm filter for air sterilization. Temperature control was achieved by placing the flask in thermostat control water bath. The 3 L of fermentor medium was inoculated with 0.2 L starting culture and growth for 24 hours with maximal agitation, 400 RPM, at 19° C., 25° C., or 30° C., with air flow set to 0.2 L/h. By the next day, after cell growth stopped at the $OD_{600}$~3-4, induction of protein synthesis was initiated by adding 0.5% methanol daily in batch mode. After 6 days of methanol induction, cells were harvested and used for membrane preparation. The limit of $OD_{600}$ obtained during growth of *P. pastoris* integrants in spinner flasks was ~25 and yield of a $\alpha 1\beta 1$ obtainable from spinner flasks was ~0.5 mg of protein per liter of culture.

The *P. pastoris* was also grown in a Bioflo-110 fementor, or bioreactor, (New-Brunswick, N.J.) with a volume capacity of up to 7 liters. A 5 ml starter containing 1% glycerol/100 mM potassium phosphate pH 6/yeast nitrogen base (Difco, Kansas City) (BMG medium) was inoculated with the porcine $\alpha 1\beta 1$ transformant and grown at 30° C. until the stationary state (36 hr). This starter was then used to inoculate a 200 ml BMG starter. The latter was grown to $OD_{600}$ 2-6, and was used as an inoculum for 3-8 liters of BMG medium (with 3% glycerol) or Basal salt medium plus trace elements (with 4% glycerol). Dissolved oxygen ($dO_2$) and pH (5.9) were controlled throughout the fermentation by manually changing airflow rate and agitation, and titrating pH with 5% ammonium hydroxide. After c. 36 hours, the glycerol in the medium was exhausted, as confirmed by a relatively rapid increase of $dO_2$ to initial values. At this point cell density reached an $OD_{600}$ of 60-70. Then a c. 4 hr fed batch stage was introduced in which 50% glycerol (15 ml/l/hr) was added continuously and the $dO_2$ was maintained at 35-40% of initial $dO_2$. After the feeding was stopped $dO_2$ rose to the initial level. The $OD_{600}$ was 100-120. Protein expression was then initiated at 25° C., either by adding a bolus of 0.5% total-fermentor-volume of methanol, three times daily, or by an initial bolus of 0.5% methanol and then continuous methanol feed of 1-2 ml/hour per 3 L of culture. YNB to 1.34% plus biotin was also added (as in the BMG medium). After 2 days of induction cells were harvested by centrifugation, washed twice in 1.4 M sorbitol/10 mM MOPS-TRIS pH 7.2/1 mM EDTA-4Na and frozen to –20° C. Wet cell weight (WCW) at the end of 2 days was 70-100 gr./liter of medium.

*P. pastoris* Membrane Preparations.

Cells were broken with glass beads and membranes were prepared as described in Cohen et al (Cohen et al., 2005, J Biol Chem, 280, 16610-16618), including a step involving treatment with 2M urea. Membranes were stored at –80° C. in MOPS-Tris, 10 mM pH 7.2; EDTA, 1 mM; glycerol, 25% with protease inhibitors. Roughly 1 g of membrane protein is obtained per 100 g cells.

Renal $Na^+,K^+$-ATPase was prepared as described in (Jorgensen, P. L. (1988) Methods Enzymol, 156, 29-43)

Purification of Recombinant $Na^+,K^+$-ATPase

Urea-treated membranes were homogenized with n-dodecyl-$\beta$-maltoside (DDM:protein, 2:1 w/w) (cat. No D310, Anatrace) in a medium containing NaCl, 250 mM; Tris.HCl, 20 mM pH 7.4; imidazole, 5 mM; PMSF, 0.5 mM; and glycerol, 10%. The protein concentration could be varied from 1-5 mg/ml and DDM adjusted accordingly from 2-10 mg/ml respectively. The unsolubilized material was removed by ultracentrifugation. Purification was done by metal-chelate chromatography using BD Talon, metal affinity resin ($Co^{2+}$-chelate). The DDM-solubilized membranes were incubated overnight at 4° C. with BD Talon beads, at a ratio of 100 µl beads per supernatant from 10 mg of membranes. EDTA was added at 50-250 µM at protein concentrations 1-5 mg/ml, respectively. The beads were washed twice for five minutes with vortexing with five volumes of a solution containing NaCl, 100 mM; Tris.HCl, 20 mM pH 7.4; C12E8, 0.1 mg/ml; DOPS or SOPS 0.05 mg/ml or other lipids and cholesterol at 0.01 mg/ml, as indicated; glycerol, 10%, and imidazole, 10 mM. Protein was eluted by mixing the beads for 40 minutes at 0° C. with one volume of a solution containing imidazole, 150 mM; NaCl, 100 mM; Tris.HCl, 20 mM pH 7.4, C12E8, 0.1 mg/ml; DOPS, or SOPS 0.05 mg/ml or other lipids and cholesterol as indicated; glycerol, 10%. The eluted protein was stored at 0° C. Preparations can be upscaled to produce about 1 mg of purified protein from 1 g. of membranes. Protein concentration was determined by comparative gel densitometry with pig kidney $Na^+,K^+$-ATPase or by Lowry assay.

Phospholipids dissolved in choloroform were dried in a stream of nitrogen and dissolved at 5 mg/ml in C12E8 10 mg/ml. Cholesterol was dissolved at 0.1 mg/ml in 1 mg/ml C12E8.

In Vitro Reconstitution of the $\alpha/His_{10}$-$\beta$/PLM Complex

Membranes expressing PLM in pHIL-D2 were solubilized in DDM (DDM:protein, 2:1 w/w), and concentrated by ultrafiltration (Centriprep YM-30 cat. No 4322 by Amicon, Millipore) at 1500 g for 2 hours at 4° C. The retentate fraction containing PLM in micelles was then incubated overnight at 4° C. with BD-Talon beads pre-bound with the $\alpha_1His_{10}\beta_1$ or $\alpha_2His_{10}\beta_1$ complex. The $\alpha$ or $\beta$/PLM complexes formed were then eluted as described above (Lifshitz et al., 2006, J. Biol. Chem., 281, 15790-15799).

SDS-PAGE, Western Blots and Immunoprecipitation.

2-5 µg of recombinant enzyme or 40 µg of yeast membranes were separated on 7.5%, or 10% polyacrylamide SDS-Tricine gels (Schagger and von Jagow, 1987, Anal Biochem, 166, 368-379). Gels were stained with Coomassie, scanned with an imaging densitometer (GS-690, BioRad) and analyzed using the Multi-analyst software (BioRad). Immunoblots were blotted with anti-KETYY antibody that recognizes the C-terminus of the $\alpha$ subunit, or with anti-$\beta$ antibodies raised against the extra-cellular domain of the $\beta$ subunit (Capasso et al., 1992, J Biol Chem, 267, 1150-1158).

Na,K-ATPase Assay $Na^+,K^+$-ATPase assays were done as described in (Cohen et al., 2005, J Biol Chem, 280, 16610-16618; Strugatsky et al., 2003, J Biol Chem, 278, 46064-46073). 0.1-0.2 µg of purified protein was incubated at 37° C. for 2-10 min in 0.1 ml of Na,K-ATPase reaction medium containing 130 mM NaCl; 20 mM KCl; 3 mM $MgCl_2$; 25 mM Histidine pH 7.4. The reaction was started by addition of 2 mM ATP [$^{32}$P-ATP]. Ouabain, digoxin or neriifolin were added to the reaction medium at the appropriate concentrations just prior to addition of ATP.

Ouabain Binding to Yeast Membranes

100 µg of membranes were incubated at 37° C. for 1 hour in 100 g of oubain binding buffer (10 mM Tris-Cl, pH 7.2, 3 mM $MgCl_2$, 1 mM vanadate-Tris, and 1 mM EGTA) in the presence of 400 nM $^3$H ouabain (Amersham). The reaction was stopped by adding 3 ml ice cold 10 mM Tris-Cl pH 7.2. The suspension was transferred to membrane filters (Whatmann GF/F). The filter was washed twice with 3 ml 10 mM Tris-Cl pH 7.2, and then taken for scintillation counting.

Materials:

BD Talon metal affinity resin (Cat. 635503) was obtained from Clontech; n-DODECYL-b-D-MALTOPYRANOSIDE, ANAGRADE® (Catalog Number: D310); OCTAETHYLENE GLYCOL MONODODECYL ETHER, ANAGRADE® (C12E8) (25% W/W) (Cat. 0330) were from Anatrace. Synthetic lipids: 1,2-Dimyristoyl-sn-Glycero-3-[Phospho-L-Serine] (Sodium Salt) DMPS; 1,2-Dipalmitoyl-sn-Glycero-3-[Phospho-L-Serine] (Sodium Salt) (DPPS); 1,2-Distearoyl-sn-Glycero-3-[Phospho-L-Serine] (Sodium Salt) (DSPS); 1,2-Dioleoyl-sn-Glycero-3-[Phospho-L-Serine] (Sodium Salt) (DOPS cat. no. 830035)); 1-Palmitoyl-2-Oleoyl-sn-Glycero-3-[Phospho-L-Serine] (Sodium Salt) (POPS); I-Stearoyl-2-Oleoyl-sn-Glycero-3-[Phospho-L-Serine] (Sodium Salt) (SOPS); 1,2-Dioleoyl-sn-Glycero-3-Phosphoethanolamine (DOPE); 1,2-Dioleoyl-sn-Glycero-3-Phosphoinositol (Ammonium Salt); 1,2-Dioleoyl-sn-Glycero-3-Phosphocholine (DOPC, cat. 850375), were obtained from Avanti and stored as chloroform solutions. Ouabain, digoxin, neriifolin, cholesterol and ergosterol were purchased from Sigma. $^{32}$ P-ATP and $^3$H-ouabain were obtained from Amersham. Recombinant Endo-H (400,000 units/mg, cat. no. P0702S) was obtained from Bio Labs. All other materials were of analytical grade. Recombinant Endo-H (400,000 units/mg, cat. no. P0702S) was obtained from Bio Labs.

Example 1

A New Purification Procedure for Na,K-ATPase expressed in *Pichia Pastoris*

Results

Figure 1:
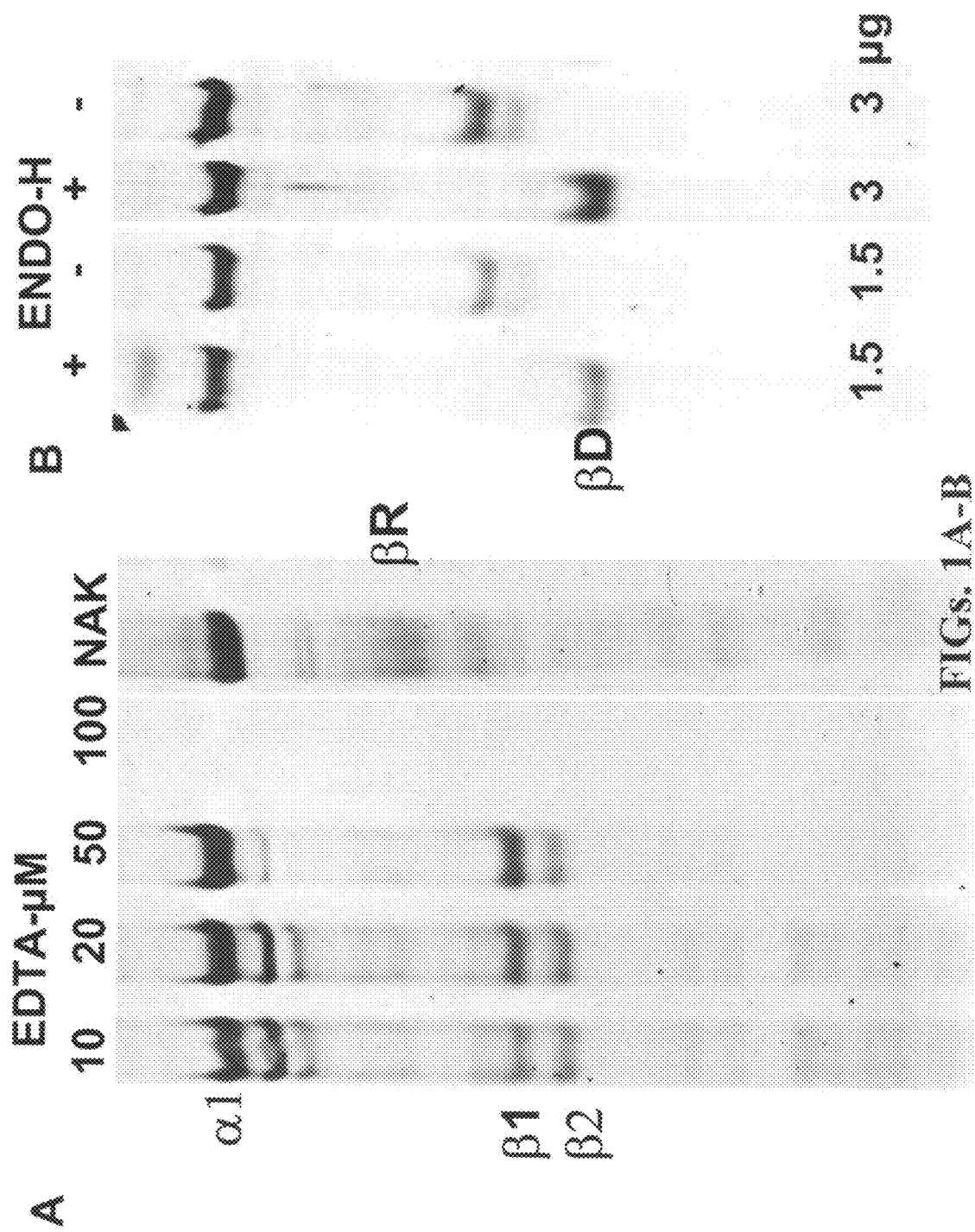

The experiment in FIG. 1 presents results of a greatly improved purification method for porcine $\alpha_1\beta_1$, which was used for all subsequent purification of human isoforms. This procedure provided up to c. 90% pure protein in a single batch step, without an HPLC step. The non-ionic detergent C12E8 was used as the washing and elution buffers. *P. pastoris* membranes expressing porcine $\alpha_1\beta_1$ were homogenized with DDM (2:1 DDM:protein mg/ml:mg/ml) and following centrifugation of the insoluble material, the soluble fraction was incubated overnight at 4° C. with BD Talon beads (Co-chelate) (100 µl beads for 10 mg membrane protein). The beads were washed twice with five volumes of a solution containing imidazole, 10 mM NaCl 100 mM, Tricine pH 7.5, 10 mM, C12E8 0.1 mg/ml, DOPS 0.05 mg/ml and glycerol 10%. The protein was eluted from the beads with one volume of the wash solution containing imidazole (150 mM) and stored at 0° C. The protein can also be frozen at −70° C. after raising the glycerol concentration to 25% w/v.

FIG. 1A shows an important feature of the purification, namely that inclusion of low concentrations of EDTA in the incubation medium reduces binding of contaminant proteins to the BD-Talon beads and improves purity. The eluted protein consists of the $\alpha_1$ subunit, two lightly glycosylated species of the $\beta_1$ subunit described previously in (Cohen et al., 2005, J Biol Chem, 280, 16610-16618), as well as minor contaminants. With 50 µM EDTA the protein purity is about 80% (lane 3) (judged by scanning and estimating the Coomassie stain of $\alpha$ and $\beta$ subunits compared to the stain of the entire lane). The EDTA must be titrated carefully, for excessively high concentrations (100 µM) remove Co from the beads and no protein is eluted (lane 4). Higher concentrations of DDM and membrane protein can also be used for the initial solubilization. In this case, higher concentrations of EDTA must be used, in proportion to the concentration of membrane protein (e.g. 300 µM EDTA with 5 mg/ml protein:10 mg/ml DDM). FIG. 1B illustrates that the sugars are easily removed from the two species of β subunit by incubation overnight with ENDO-H. The result is a preparation consisting only of α and deglycosylated β subunit. In this experiment the contaminant band below the α subunit was not seen and the protein was c.90% pure. Mass spectrometry showed that the average mass of $\beta_1$ and $\beta_2$ are 44, 386±271 and 42,644±9.6 respectively, while that of PD is 38,396.2±164, which is close to the predicted value of the fully deglycosylated β subunit with the 10*His tag (Cohen et al., 2005, J Biol Chem, 280, 16610-16618).

The concentration of $\alpha_1\beta_1$ protein complex eluted from the beads was conveniently determined by comparing Coomassie stain of the α subunit with that of a standard amount of partially purified pig kidney Na,K-ATPase (FIG. 1A, lane 5,). Note, however, that the purity of the pig kidney Na,K-ATPase is only about 40%. Comparison of purities of recombinant and renal Na,K-ATPase shows that the estimate of the true amount of recombinant protein is almost exactly 2-fold lower than estimated from the renal Na,K-ATPase standard. Direct estimation of recombinant protein by Lowry assay confirms this correction factor, although usually Lowry assays are not done for pilot experiments in order to save protein. Amino acid analyses show that the Lowry assay overestimates the concentration of protein by about 10%. Taking these corrections into account, the true concentration of eluted protein is 0.1-0.3 mg/ml, and 15-25 µg are obtained from 10 mg membrane protein.

A normal 3 liter fermentor run (see Methods) produced about 250-350 g of *P. pastoris* cells and 2-3 g of membrane protein. The purification procedure can easily be upscaled for 100 mg and 1 g quantities of membrane protein. The yield is about 1 mg of purified Na,K-ATPase per gram of membrane protein. This amount suffices for at least one thousand of standard Na,K-ATPase activity assays (see below).

Example 2

Expression of Human $\alpha_1$ and $\alpha_2$ Isoforms and Purification of $\alpha_1\beta_1$ and $\alpha_2\beta_1$ Complexes Results Human $\alpha_1/\alpha_2$ porcine $\beta_1$ subunits were expressed together in *P. pastoris* exactly like porcine $\alpha_1\beta_1$ as described in (Cohen et al., 2005). FIG. 2A shows immunoblots detecting human $\alpha_2$ expressed with porcine $\beta_1$ subunit in different conditions, and optimization of expression. In the first set of Mut$^S$ recombinants selected, essentially no expression of $\alpha_2$ was seen at the normal temperature of 25° C. (FIG. 2A, lane 3). However, when the yeast were grown at lower temperatures some expression was seen at 15° C. and more at 20° C., for one clone "a". By comparison, the best clone of human $\alpha_1$ porcine $\beta_1$ showed much higher levels of expression (FIG. 2A lanes 4,5), and even higher levels when grown at the normal 25° C. (not shown). This fits the previous findings that pig $\alpha_1\beta_1$ is expressed optimally at 25° C. (Strugatsky et al., 2003, J Biol Chem, 278, 46064-46073). FIG. 2B shows that the time-course of methanol-induced expression is quite similar for $\alpha_2$ and $\alpha_1$. Although expression levels were optimal within 24 hours of induction with methanol, normally, both $\alpha_1$ and $\alpha_2$ were induced for 4-5 days in order to increase biomass. The most important optimization step for $\alpha_2$ expression was made by screening a much larger number of Mut$^S$ clones than in initial experiments, and growing the clones at 20° C. Previously the present inventors have shown a large variability in expression of the α subunit in different Mut$^S$ clones, and that the highest level of expression reflects the highest copy number of the incorporated α and β genes. Thus a total of 50 $\alpha_2$ clones were screened after induction with methanol at 20° C. Several clones were found to express much higher levels than the clone "a" analyzed initially. FIG. 2C shows an example of this variability. Clone "b" and "d" were grown in spinner flasks and membranes prepared. The immunoblot in FIG. 2E shows that somewhat lower but still comparable amounts of $\alpha_2$ subunit was expressed in "b", as in the best clone of the human and porcine $\alpha_1$. Ouabain binding capacity in the $\alpha_2$ clone "b" (15.32 pmoles/mg) was only a little lower than in the human $\alpha_1$ clone (19.82 pmoles/mg), while that in clone "d" was lower (6.33 pmoles/mg). Thus clone "b" of human $\alpha_2$ was chosen for all subsequent studies.

*P. pastoris* clones expressing human $\alpha_1$ porcine $\beta_1$ and human $\alpha_2$ porcine $\beta_1$ were grown in the fermentor or Spinner flasks at 25° C. or 20° C., respectively, membranes were prepared, and the proteins were purified by the one-step procedure described in FIG. 1. FIG. 3 shows that very similar purification of human $\alpha_1\beta_1$ and $\alpha_2\beta_1$ were observed as for porcine $\alpha_1\beta_1$, although the amount of $\alpha_2\beta_1$ was somewhat lower than for either type of $\alpha_1\beta_1$ complex. Purification of both human $\alpha_1$ and $\alpha_2$ subunits via the 10*His tag at the N-terminus of the porcine $\beta_1$ subunit shows that the α and β subunits are interacting in $\alpha_1\beta_1$ and $\alpha_2\beta_1$ complexes.

Human $\alpha_1$ and $\alpha_2$ subunits were expressed together with the human $\beta_1$ and also $\beta_3$ subunits. Examples of screens of Mut$^S$ clones are shown in FIG. 4. These show a typical pattern of varied levels of expression of the α subunits, and indicate that the human $\alpha_1$ subunit is interacting with the human $\beta_1$ or $\beta_3$ subunits, as expected. The all human $\alpha_1\beta_1$, $\alpha_2\beta_1$ and $\alpha_1\beta_3$ complexes have not yet been purified.

Example 3

Na,K-ATPase Activity of Human $\alpha_1\beta_1$ and $\alpha_2\beta_1$ Complexes

Results

The Na,K-ATPase activity at 37° C. of the purified human $\alpha_1$ porcine $\beta_1$ and human $\alpha_2$ porcine $\beta_1$ complexes has been compared with that of porcine $\alpha_1\beta_1$ (FIG. 5). The protein eluted from the BD Talon beads was diluted 50-100-fold into the Na,K-ATPase reaction medium without addition of C12E8 and DOPS. Note that the 32Pi release is quite linear for 10 minutes and the order of reactivities appears to be human $\alpha_1\beta_1$>pig $\alpha_1\beta_1$>human $\alpha_2\beta_1$. It is important that C12E8 and DOPS is not added to the ATPase reaction mixture, for the detergent inactivates the protein. As expected (and see FIG. 15 below) the activity was inhibited by ouabain and other cardiac glycosides. The range of specific activities in different experiments is provided in Table 2 hereinbelow.

TABLE 2

| | |
|---|---|
| Human α1β1 | 8-16 µmoles/min/mg protein |
| Porcine α1β1 | 8-12 µmoles/min/mg protein |
| Human α2β1 | 6-10 µmoles/min/mg protein |

These specific activities are lower than the specific activities of purified renal Na,K-ATPase (35-45 µmole/min/mg (Jorgensen, 1988, Methods Enzymol, 156, 29-43)).

Example 4

Stabilization of $\alpha_1\beta_1$ and $\alpha_2\beta_1$ Complexes by Phospholipids and Cholesterol As reported by the present inventors (Cohen et al., 2005, J Biol Chem, 280, 16610-16618), the presence of DOPS in the washing and elution buffers is necessary in order to maintain a enzymatically active complex. The purification procedure produces a preparation, which is ideally suited for testing the specificity of the phospholipid requirements.

FIG. 6A shows an experiment with porcine $\alpha_1\beta_1$ showing activity is maintained in the order DOPS>DOPI>>DOPE and essentially no activity is observed without added phosopholipid. DOPC also leads to porcine $\alpha_1\beta_1$ complexes with somewhat lower initial Na,K-ATPase activity at 37° C. than for DOPS. As seen in Table 3, hereinbelow, for human $\alpha_1\beta_1$, initial Na,K-ATPase activities with DOPS and DOPC are similar. FIG. 6B shows a concentration dependence of DOPS and DOPI, and shows that DOPS is effective at somewhat lower concentrations. Both DOPS and DOPI are acid phospholipids, while DOPC and DOPE have no net charge.

TABLE 3

| Phospholipid | Na, K-ATPase activity µmoles/min/mg |
|---|---|
| DOPS | 11.64 |
| DOPS cholesterol | 14.04 |
| DOPC | 14.28 |
| DOPC cholesterol | 12.4 |

The requirements for the acid phospholipid DOPS is not absolute in the sense that DOPI and also DOPC, but not DOPE, sustain Na,K-ATPase activity immediately following elution from the beads. However, there is a very large effect of the phospholipid type on the stability of the protein i.e the maintenance of Na,K-ATPase activity over time. The present inventors have shown previously that DOPS preserves Na,K-ATPase activity of porcine $\alpha_1\beta_1$ activity much better than DOPC at 0° C., particularly when the protein is prepared in a K-medium or following deglycosylation (Cohen et al., 2005, J Biol Chem, 280, 16610-16618). In agreement with the latter, FIGS. 9A-C, which is concerned primarily with effects of cholesterol, also show that at 37° C., Na,K-ATPase activity of human $\alpha_1\beta_1$ is also much more labile when prepared in DOPC compared to DOPS. Thus the necessity for the acid phospholipid is for preservation against inactivation of the protein.

FIGS. 7 and 8A-B present remarkable observations, namely that the stability of the protein is optimal with phosphatidyl serine containing one unsaturated (sn2 position) and one saturated (sn1) fatty acid side chain. The experiment in FIG. 7 compared the stability with different chain lengths and saturation of the side chains. As shown in Table 4 below, all six phosphatidyl serines sustained Na,K-ATPase activity when measured immediately after elution from the BD Talon beads, albeit lower for DSPS and DPPS than for the others. However, the clear-cut result is that for all three phosphatidyl serines with all saturated side chain (C14, C16 or C18) activity was rapidly lost at 0° C. By contrast with phosphatidyl serines having at least one unsaturated oleoyl chain in the sn2 position Na,K-ATPase activity was preserved much better and declined relatively slowly at 0° C.

TABLE 4

| NKA activity | DSPS | DPPS | DMPS | DOPS | SOPS | POPS |
|---|---|---|---|---|---|---|
| µmoles/min/mg | 4.72 | 6.46 | 11.48 | 11.42 | 11.92 | 12.58 |

FIG. 7 also showed that stability of Na,K-ATPase with SOPS declined even more slowly than with the standard DOPS used in all previous experiments. FIGS. 8A-B show indeed that SOPS is significantly more stabilizing than DOPS both at 37° C. and 0° C. At 37° C. the activity rose significantly before declining. This may be indicative of an equilibration of the protein with the lipid prior to the thermal inactivation process. Thus, SOPS has now become the phosphatidyl serine of choice even though most experiments were done with DOPS.

FIG. 9A show that the presence of a low concentration of cholesterol greatly stabilizes the Na,K-ATPase activity of human $\alpha_1\beta_1$ when prepared with either DOPS or DOPC, even though the initial activity following elution from the beads is not appreciably different in the three conditions (See Table 3, hereinabove). A similar effect has been seen for porcine $\alpha_1\beta_1$ (FIG. 10). FIG. 9B shows that the stabilizing effect is rather specific since the plant and yeast steroid ergosterol has only a minor stabilizing effect compared to the cholesterol (compare the structures in FIG. 9C). The large stabilizing effect on human and porcine $\alpha_1\beta_1$ is seen when the protein is incubated at 37° C. but at 0° C. only a minor effect is seen due to the fact that activity is fairly stable even without cholesterol (see human $\alpha_1\beta_1$ in FIG. 11). FIG. 10 shows another important finding that cholesterol is unable to sustain Na,K-ATPase in the absence of a phospholipid such as SOPS, while activity is fully stabilized at 37° C. for two hours in the presence of SOPS. Thus, the stabilizing effect of cholesterol requires the presence of SOPS.

In contrast to the purified human and porcine $\alpha_1\beta_1$ complexes, which are relatively stable at 0° C., the human $\alpha_2\beta_1$ complex was very unstable, losing activity at 0° C. with a half-time of about 1-2 days (FIG. 11). This preparation is not useful for any systematic work to characterize its properties, inhibitor interactions etc. The important finding in FIG. 12 is that the presence of a low concentration of cholesterol together with DOPS greatly stabilized the $\alpha_2\beta_1$ complex at 0° C. Another experiment showed that ergosterol is much less effective than cholesterol (not shown). FIG. 12 documents that the combination of SOPS/cholesterol is superior to DOPS/cholesterol, as found also for $\alpha_1\beta_1$. With SOPS/cholesterol the half-time for loss of activity at 0° C. is about 20-30 days. It is of interest that even in the presence of cholesterol, $\alpha_2\beta_1$ is much less stable than $\alpha_1\beta_1$. This is seen best at 37° C. (FIG. 13). Nevertheless, the stabilization afforded by the SOPS/cholesterol combination suffices for routine work with $\alpha_2\beta_1$, such as for testing of inhibitor effects, as described below.

Example 5

Stabilization of $\alpha_1\beta_1$ and $\alpha_2\beta_1$ Complexes by FXYD1

FXYD proteins are subsidiary sub-units of Na,K-ATPase which modulate its activity. Recently, the present inventors have shown that human FXYD1, also known as phospholemman or PLM, which is expressed in cardiac and other muscle tissues, can be co-expressed with porcine $\alpha_1\beta_1$ subunits or expressed separately and re-constituted with $\alpha_1\beta_1$ in vitro leading to the $\alpha_1\beta_1$/FXYD1 complex (Lifshitz et al., 2006, J. Biol. Chem., 281, 15790-15799). The functional properties of the $\alpha_1\beta_1$/FXYD1 complex are different from $\alpha_1\beta_1$, primarily in the apparent affinity for Na ions.

Figure 15:
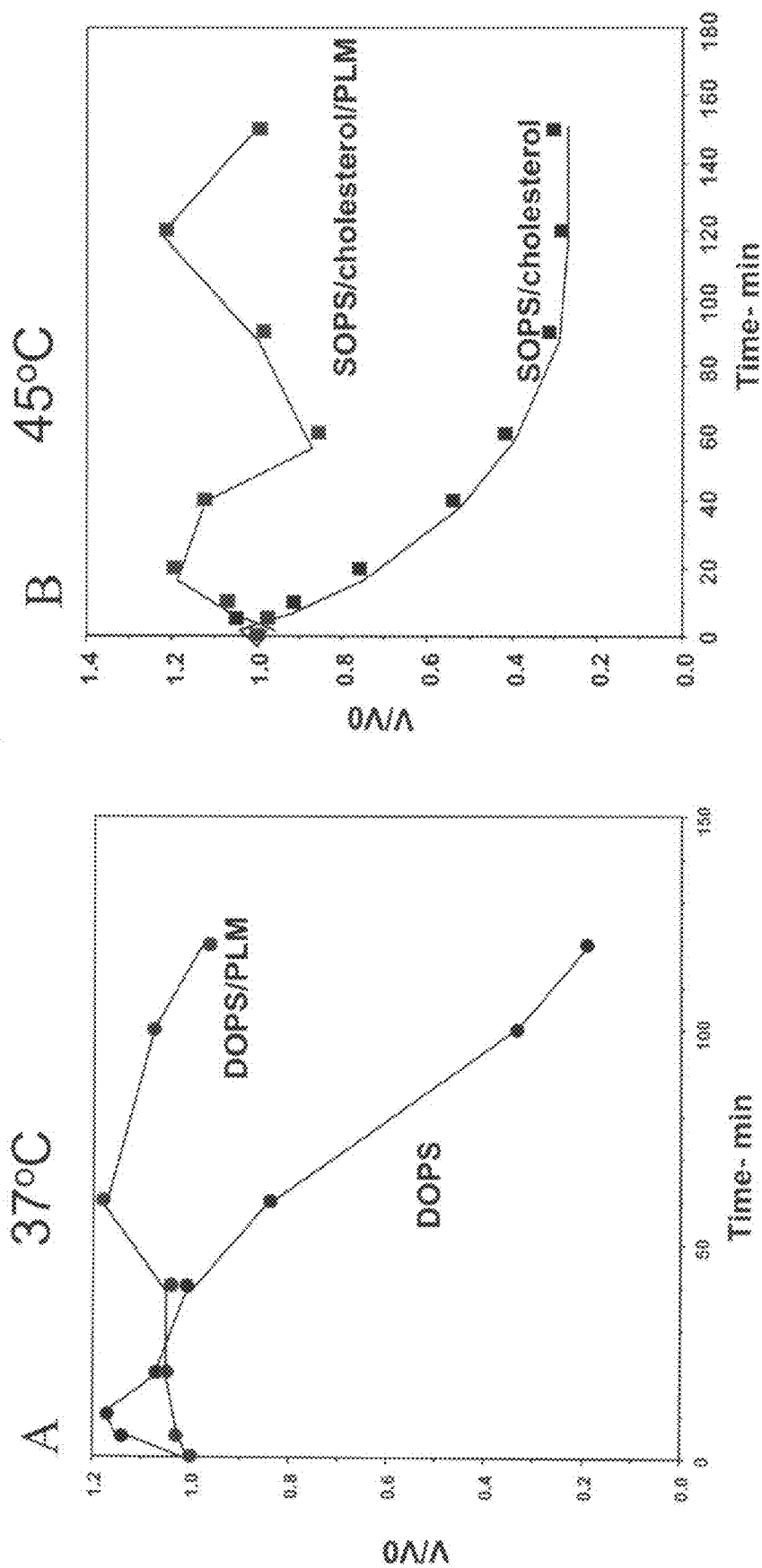

The data in FIGS. 14-16 show striking findings with human $\alpha_1\beta_1$ and $\alpha_2\beta_1$, which are both unexpected and highly significant for the present purpose. In preliminary experiments (not shown) PLM was found to be reconstituted together with human $\alpha_1\beta_1$ and $\alpha_2\beta_1$, in vitro, as found previously with porcine alp). In the experiment in FIG. 14 the purified human $\alpha_1\beta_1$ complex was prepared in the presence of different concentration of DOPS, with or without PLM. The striking finding is that the Na,K-ATPase activity of the eluted $\alpha_1\beta_1$/FXYD1 complex is independent of added DOPS in the washing and elution buffers, whereas addition of DOPS is essential for maintaining activity without the PLM. The DDM-solubilized PLM is concentrated up to 3-fold prior to reconstitution and it is possible that endogenous yeast lipid is also concentrated. However, it is unlikely that presence of a higher amount of yeast lipids with the PLM can explain the redundancy of exogenous DOPS in the wash and elution buffers since it has been observed that addition of added exogenous DOPS during binding to the BD-Talon beads does not obviate the need to add DOPS to the subsequent wash and elution buffers, showing the lipid added in the binding step is washed away by the detergent in the absence of added DOPS (experiment not shown). A likely explanation of the finding in FIG. 14 is that the interacting PLM stabilizes endogenous yeast-derived PS on the protein. A further implication of the finding and explanation is that PLM could stabilize the complex against thermal inactivation. The latter prediction was tested in the experiments of FIGS. 15A-B and FIG. 16. In FIGS. 15A-B human $\alpha_1\beta_1$ was prepared either with DOPS or with the combination of SOPS/cholesterol, which maximally stabilizes $\alpha_1\beta_1$ or $\alpha_2\beta_1$. Aliquots of the preparations were incubated either at 37° C. or 45° C., respectively, for the indicated times, and then returned to 0° C., prior to measurement of Na,K-ATPase activity. For the preparation made with DOPS, activity was lost with a half-time of about 70 minutes falling to c. 20% of initial activity after 120 minutes at 37° C. In the presence of PLM, there was essentially no loss of activity up to 120 minutes. When prepared with SOPS/cholesterol, activity of the control without PLM was stable for 120 minutes at 37° C. (not shown). Thus it was necessary to raise the temperature to 45° C. to observe thermal inactivation. In this condition the Na,K-ATPase activity of the $\alpha_1\beta_1$ complex made with PLM was essentially stable over 150 minutes at 45° C. The $\alpha_2\beta_1$ complex was prepared with SOPS/cholesterol without and with PLM and, as seen in FIG. 16, the activity without PLM was inactivated with a half-time of approximately 20 minutes, while the preparation made with PLM was essentially stable for 60 minutes at 37° C. Thus, unexpectedly, these experiments reveal a very large stabilizing effect of the FXYD1 on both $\alpha_1\beta_1$ and $\alpha_2\beta_1$.

Example 6

Effects of Cardiac Glycosides on Human $\alpha_1\beta_1$ and $\alpha_2\beta_1$

FIGS. 17A-B and 18A-B document inhibition of Na,K-ATPase activity of human $\alpha_1\beta_1$ and $\alpha_2\beta_1$ at 37° C. by ouabain, digoxin and neriifolin. The inhibitor was added directly to the reaction medium at 37° C. immediately prior to addition of ATP, which starts the reaction.

In FIG. 17A the reaction was carried out for 10 minutes. The Na,K-ATPase activity of $\alpha_1\beta_1$ was fully inhibited with a K0.5 of 0.46±0.069 μM. Ouabain inhibited Na,K-ATPase of $\alpha_2\beta_1$ with a K0.5 of 0.098±0.009 μM and it appeared that activity was not quite fully inhibited (with an offset of 0.069±0.01). When activity was measured over 60 minutes at 37° C. (FIG. 17B), the inhibition curve for $\alpha_2\beta_1$ was unchanged (K0.5 0.107±0.015, offset 0.056±0.017), but that for $\alpha_1\beta_1$ shifted strongly to the left (K0.5 0.0246±0.0057). This time-dependent difference in apparent affinity for $\alpha_1\beta_1$ but not for $\alpha_2\beta_1$ can be explained by a finding that ouabain binds to and dissociates from $\alpha_2$ much more rapidly than to $\alpha_1$ (Crambert et al., 2000, J Biol Chem, 275, 1976-1986). Thus, one can expect inhibition of $\alpha_1$ at the short times to reflect the rate of binding of ouabain, whereas the K0.5 for ouabain at 60 minutes can be taken to reflect equilibrium binding properties in the conditions of the reaction medium. The similar K0.5 for $\alpha_2$ at either reaction time indicates that the ouabain has reached equilibrium within the 10 minutes at 37° C. Overall it appears that ouabain has some preference for $\alpha_1$ over $\alpha_2$ A similar experiment (FIG. 18A) using digoxin over 60 minutes at 37° C. shows a somewhat lower K0.5 for inhibition of $\alpha_2$ (K0.5 0.034 μM±0.0048) and an offset of 0.058±0.016 compared to inhibition of $\alpha_1$ with an K0.5 of 0.091±0.01 μM and no significant offset. Another experiment (FIG. 18B) looked at neriifolin, a cardiac glycoside from *Thevetia ahouia*, which has been shown recently to protect brain against ischemic stroke damage (Wang et al., 2006, Proc Natl Acad Sci USA, 103, 10461-10466). The K0.5 for inhibition was similar for the two isoforms and again a small but significant fraction of activity was not inhibited even at high concentrations in the case only of the $\alpha_2$ isoform ($\alpha_1$: K0.5 0.05±0.007 μM, offset=0; $\alpha_2$: K0.5 0.029±0.0041 μM, offset 0.12)

In conclusion, ouabain appears to show some preference for $\alpha_1$: (K0.5 ($\alpha_1$:—0.024 versus $\alpha_2$—0.107 μM), digoxin some preference for $\alpha_2$ (K0.5 $\alpha_1$ 0.091 versus $\alpha_2$ 0.034 μM) and neriifolin no significant $\alpha_1/\alpha_2$ preference (K0.5 $\alpha_1$ 0.050 versus $\alpha_2$ 0.029 μM), at least in the conditions of the Na,K-ATPase reaction at 37° C. Furthermore, up to 10% of the activity of (12 is not inhibited at limitingly high concentrations of the three inhibitors.

Discussion

Expression and Purification of Human $\alpha_1\beta_1$ and $\alpha_2\beta_1$ Isoforms The new one-step batch purification method described here for porcine $\alpha_1\beta_1$ and human $\alpha_1\beta_1$ and $\alpha_2\beta_1$ complexes (FIGS. 1 and 3), produces up to 80-90% pure Na,K-ATPase. This represents an important improvement compared to the published procedure (Cohen et al., 2005) due to its great convenience, efficiency and avoidance of a further size-exclusion HPLC step.

Optimal expression of the human $\alpha_2$ porcine 10His-$\beta_1$ isoform involved two important features, namely reduction of the temperature of the methanol induction phase to 20° C. from the standard 25° C., and screening of a large number of Muts clones, grown at 20° C., for high copy number transfectants, see (Strugatsky et al., 2003). Previously, unstable mutants of the $\alpha_1$ subunit have been found to be expressed in *S. Cerevisae* at 15° C. but not at the normal growth temperature of 30° C. (Jorgensen et al., 2001, J Bioenerg Biomembr, 33, 367-377). The necessity of growth of *P. pastoris* expressing $\alpha_2\beta_1$ at 20° C. rather than 25° C. is consistent with an observation that $\alpha_2\beta_1$ expressed in *S. Cerevisae* is unstable and is degraded, thus yielding a low level of expressed protein (Muller-Ehmsen et al., 2001, Am J Physiol Cell Physiol, 281, C1355-1364). The $\alpha_2\beta_1$ clone with optimal expression (15.32 pmoles ouabain bound/mg protein) has a site density almost twenty-fold higher than that described in (Muller-Ehmsen et al., 2001) (0.8 pmoles/mg). This is one crucial feature enabling purification of the $\alpha_2\beta_1$ complex.

Stabilization of Human $\alpha_1\beta_1$ and $\alpha_2\beta_1$ Complexes by Phospholipid and Cholesterol The purified Na,K-ATPase provides an ideal system for looking at specificity of lipid interactions. This has led to important insights into the mechanism and optimization of lipid effects. One major conclusion is that phospholipid and cholesterol are required for stabilization i.e. protection of the protein against time-dependent inactivation, rather than for enzyme activity per se. A second major conclusion is that both the phospholipid and cholesterol interact specifically with the protein.

The data in FIGS. 4 and 5 show that Na,K-ATPase activity is maintained linear at 37° C. for at least 10 minutes and other experiments show that $\beta_1$ release is linear for at least 1 hour (not shown). The protein is diluted about 100-fold into the reaction medium, which contains no added detergent or DOPS i.e the C12E8 concentration is diluted to far below the CMC (0.05 mg/ml). Since Na,K-ATPase activity is not observed without phospholipid in the elution buffer (FIG. 5), the maintenance of Na,K-ATPase activity in this normal reaction medium provides one piece of evidence that phospholipid (DOPS) is bound to the protein.

It has previously been shown (and corroborated in FIG. 9 of Example 4) that DOPC can sustain activity but much less effectively than DOPS when protein was eluted in the presence of K rather than Na ions, as is usually the case, or after deglycosylation (Cohen et al., 2005). The latter findings also suggested a specific interaction of the acid phospholipid DOPS with the protein. Note that the stabilizing effect of phospholipid is not absolutely specific for DOPS since DOPI is also able to sustain somewhat lower activity and with a lower apparent affinity than DOPS, while DOPE is ineffective. A strong implication of the previous and present findings is that the acid head-group of DOPS (or DOPI) interacts with the protein.

Figure 8:
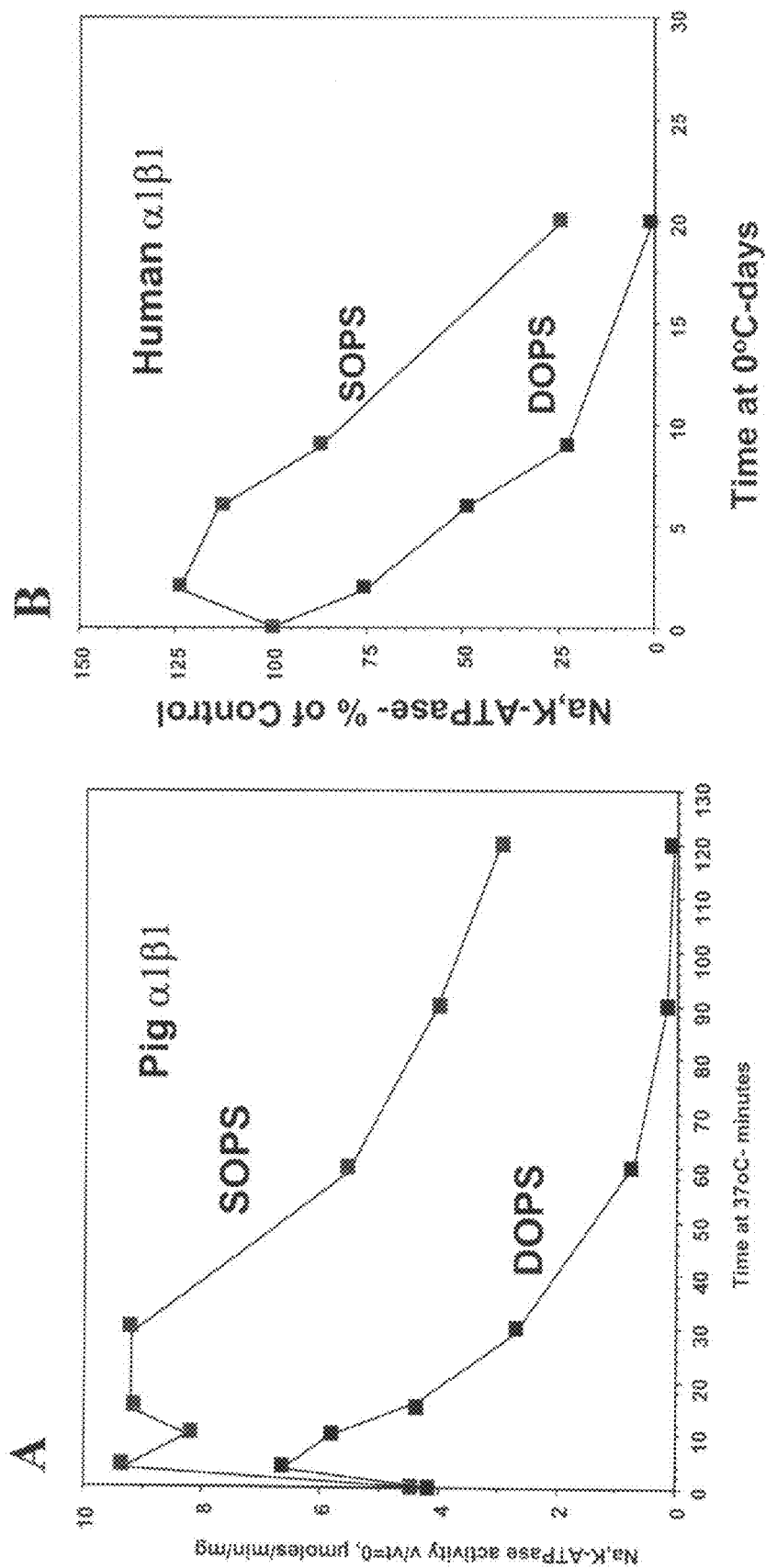

The data in FIGS. 7 and 8 show that stability of the porcine or human $\alpha_1\beta_1$ isoforms is maintained best at either 0° C. or 37° C. only with phosphatidyl serine having an unsaturated fatty acid side chain in the sn-2 position, and optimally with the asymmetric SOPS rather than the symmetric DOPS. Note, however, that although activity is rapidly inactivated with all three saturated fatty acid PS derivatives, immediately after elution from the beads, activity of saturated C14 dimyristoyl PS derivative (DMPS) and DOPS, SOPS or POPS derivative is not significantly different. That initial activity with DSSP and DPPS was lower was probably due to partial inactivation during the purification procedure. In the present series of experiments DOPC was also found to sustain a similar initial Na,K-ATPase activity as DOPS (Table 3, hereinabove) but DOPS is better at maintaining activity over time than DOPC (FIG. 9A). The conclusion from this data is that there is a clear dissociation between the ability of the phospholipid to stabilize activity over time and to maintain initial Na,K-ATPase activity, which does not depend critically on the phospholipid type. The evidently superior ability of SOPS to stabilize over time at both 0° C. and 37° C., compared to DOPS, is surprising and seems to indicate the existence of specific interactions of both the saturated (stearoyl) and unsaturated (oleoyl) side chains with the protein. A requirement for acid phospholipid to maintain detergent-soluble native renal Na,K-ATPase ($\alpha 1$ isoform) active has been observed previously (Hayashi et al., 1989, Biochim Biophys Acta, 983, 217-229) but no evidence for the specificity of the side-chains was reported and no conclusion on specific binding could be drawn.

Cholesterol has been found to strongly stabilize both porcine $\alpha_1\beta_1$ and human $\alpha_1\beta_1$ at 37° C. (shown for human $\alpha_1\beta_1$ in FIGS. 9A-B and Table 3). Loss of activity is greatly slowed by the presence of low concentrations of cholesterol with either DOPS or DOPC, although the DOPS/cholesterol combination is clearly superior. Cholesterol is the major mammalian membrane sterol, and a clear indication for selectivity of its effect is the finding that ergosterol, the principal membrane sterol in yeasts, is only poorly effective. Note, again (Table 3) that there is no significant difference in the initial activity at 37° C. with and without cholesterol, but only a large stabilizing effect. As shown in FIG. 10, cholesterol is unable to maintain activity in the absence of SOPS. At 0° C. stabilization of either porcine $\alpha_1\beta_1$ and human $\alpha_1\beta_1$ by cholesterol is not observed because the complexes are quite stable even without cholesterol (see FIG. 10). Other data show that cholesterol partially inhibits activity when it is measured at 0° C. (not shown). The findings in FIGS. 9 and 10 imply a three-way specific stabilizing interaction between the cholesterol-SOPS— $\alpha_1\beta_1$ complexes at 37° C., Indeed one can hypothezise that a physiological role of cholesterol is to stabilize $\alpha_1\beta_1$ at 37° C., the physiological temperature. Previously, both activating and inhibitory effects of cholesterol on native Na,K-ATPase ($\alpha_1$ isoforms) and Na,K-ATPase in reconstituted proteolipsomes have been reported (Cornelius, 1995, Biochim Biophys Acta, 1235, 205-212; Cornelius, 2001, Biochemistry, 40, 8842-8851; Yeagle et al., 1988, Biochemistry, 27, 6449-6452) but no conclusion as to a specific stabilizing effect at 37° C. could be drawn and no evidence for a mandatory requirement for phospholipids.

The stabilizing effect of cholesterol proved to be crucial for stabilizing a functional purified $\alpha_2\beta_1$ complex, as seen in FIGS. 11 and 12. The instability of $\alpha_2\beta_1$ already detected in whole yeast might be attributed, at least partly, to the presence of ergosterol and absence of cholesterol. The instability was detected clearly also in the purified protein, which rapidly lost activity at 0° C. when prepared with DOPS alone. In this state the preparation is difficult to work with. However, when prepared with cholesterol and DOPS or, even better, with SOPS and cholesterol the $\alpha_2\beta_1$ complex was greatly stabilized at 0° C. (FIG. 12). With SOPS and cholesterol the half-time for loss of activity at 0° C. is about 20 days.

Although the combination of SOPS/cholesterol suffices to stabilize the $\alpha_2\beta_1$ isoform sufficiently for routine work, $\alpha_2\beta_1$ is still much less stable than $\alpha_1\beta_1$ i.e there appears to be an additional source of intrinsic instability of $\alpha_2\beta_1$ (FIG. 13). What is the origin of this feature? In native muscle membranes the $\alpha_2$ has been detected in specific domains (e.g. near the T-tubules overlying the sarcoplasmic reticulum) as compared to $\alpha_1\beta_1$ which is ubiquitously distributed (Juhaszova and Blaustein, 1997, Ann NY Acad Sci, 834, 524-536). Thus, one can speculate that additional interactions with lipids (e.g sphingolipids), or proteins such as caveolins are lacking in the purified $\alpha_2\beta_1$ complex. Alternatively, differences in oligomeric structure of the isoforms could underlie the difference in stability in $\alpha_1\beta_1$ and $\alpha_2\beta_1$ complexes.

The data resented herein provides strong evidence for specific interactions between the acid phospholipids phosphatidyl serine (SOPS), cholesterol and the Na,K-ATPase. Several crystal structures of membrane protein have shown the existence of specifically bound lipids and addition of lipids aids crystallization of membrane proteins. It is becoming clear that specifically bound or "co-factor" lipids can be distinguished from the bulk of lipids which surround the transmembrane helices when the protein is normally embedded in the lipid bilayer "Annular lipids" are bound only weakly and are largely exchangeable by detergent, but "co-factor" lipids cannot be replaced without destabilizing the protein. The present data provides evidence that both the acid head group of PS and the fatty acid side-chains interact with and stabilizes the protein. The strong synergism between cholesterol and DOPS or SOPS in stabilizing the enzyme, selectivity for cholesterol over ergosterol and lack of effect of cholesterol alone, suggests that cholesterol may interact with the protein and the SOPS in the vicinity of the SOPS interaction site.

To summarise, this work has revealed essential stabilizing interactions of both PS (especially SOPS) and cholesterol with both $\alpha_1\beta_1$ and $\alpha_2\beta_1$ isoforms. These interactions are not at all predictable. Analysis of the stabilizing effects of phospholipids and cholesterol has been crucial in the development of the purified functional $\alpha_1\beta_1$ and, especially $\alpha_2\beta_1$ complexes.

Stabilization of Human $\alpha_1\beta_1$ and $\alpha_2\beta_1$ complexes by FXYD1

The findings that reconstitution of the $\alpha\beta$ complex with FXYD1 (PLM) obviates the need to add exogenous phospholipid could imply either that PMS mimics the role of the phosphatidyl serine or, more likely, that PLM stabilizes the interaction of endogenous phosphatidyl serine with the protein. The very strong stabilization of both detergent-soluble $\alpha1\beta1$ and $\alpha2\beta1$ complexes by PLM is an unpredictable effect of the FXYD protein.

Inhibition of $\alpha_1\beta_1$ and $\alpha_2\beta_1$

The inhibition curves of ouabain, digoxin and neriifolin show that both $\alpha_1\beta_1$ and $\alpha_2\beta_1$ are strongly inhibited at low sub-micromolar concentrations and even moderate differences in K0.5 can be comfortably detected. Specifically, $\alpha_1\beta_1$ appears to be about 3-4-fold more sensitive than $\alpha_2\beta_1$ to ouabain and $\alpha_2\beta_1$ appears to be about 3-fold more sensitive than $\alpha_1\beta_1$ to digoxin. In addition $\alpha_2\beta_1$ seems to be only 90-95% inhibited by all three inhibitors. At present it is not known if this represents a true molecular feature of the interaction of $\alpha_1\beta$ with the cardiac glycosides or the presence of a small amount of a contaminating ATPase.

CONCLUSION

The experimental system for expressing, purifying, and stabilizing human and $\alpha_1\beta_1$ and $\alpha_2\beta_1$ isoforms of Na,K-ATPase in a functional state provides a ready source of the purified isoforms, which should be highly suited for high through-put studies (HTS) of libraries of inhibitors, in the quest for an $\alpha_2$-specific inhibitor. Such screens may also identify compounds with better binding characteristics to both $\alpha_1$ and $\alpha_2$ isoforms compared to conventional cardiac glycosides, and also antagonists of cardiac glycosides, which compete for binding but do not inhibit Na,K-ATPase activity or inhibitors which are affected by the presence of FXYD1 or affect $\alpha\beta$-FXYD1 interactions.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A composition of matter comprising catalytically active Na,K-ATPase, said Na,K-ATPase comprising an $\alpha$ and $\beta$ subunit, said Na,K-ATPase being at least 85% purified, wherein said Na,K-ATPase comprises a human $\alpha_1$ subunit and a porcine $\beta_1$ subunit.

2. A composition of matter comprising catalytically active Na,K-ATPase, said Na,K-ATPase comprising an $\alpha$ and $\beta$ subunit, said Na,K-ATPase being at least 85% purified, wherein said Na,K-ATPase comprises a human $\alpha_2$ subunit and a porcine $\beta_1$ subunit.

3. A composition of matter comprising catalytically active Na,K-ATPase, said Na,K-ATPase comprising an $\alpha$ and $\beta$ subunit, said Na,K-ATPase being at least 85% purified, wherein said Na,K-ATPase comprises a porcine $\alpha_1$ subunit and a porcine $\beta_1$ subunit.

4. The composition of matter of claim 1, further comprising phospholipids.

5. The composition of matter of claim 4, wherein said phospholipids are SOPS.

6. The composition of matter of claim 4, further comprising cholesterol.

7. The composition of matter of claim 1, further comprising FXYD.

8. The composition of matter of claim 1, wherein a half-life for loss of activity at 0° C. of said Na,K-ATPase is at least 20 days.

9. The composition of matter of claim 2, further comprising phospholipids.

10. The composition of matter of claim 9, wherein said phospholipids are SOPS.

11. The composition of matter of claim 9, further comprising cholesterol.

12. The composition of matter of claim 3, further comprising phospholipids.

13. The composition of matter of claim 12, wherein said phospholipids are SOPS.

14. The composition of matter of claim 12, further comprising cholesterol.

15. The composition of matter of claim 2, further comprising FXYD.

16. The composition of matter of claim 3, further comprising FXYD.

17. The composition of matter of claim 2, wherein a half-life for loss of activity at 0° C. of said Na,K-ATPase is at least 20 days.

18. The composition of matter of claim 3, wherein a half-life for loss of activity at 0° C. of said Na,K-ATPase is at least 20 days.

* * * * *